(12) United States Patent
Harwood et al.

(10) Patent No.: US 8,044,173 B2
(45) Date of Patent: Oct. 25, 2011

(54) ASYMMETRIC SYNTHESIS OF PEPTIDES

(75) Inventors: Laurence M. Harwood, Berkshire (GB); Ran Yan, Berkshire (GB)

(73) Assignee: University of Reading, Berkshire, Reading (GB)

( * ) Notice: Subject to any disclaimer, the term of this patent is extended or adjusted under 35 U.S.C. 154(b) by 375 days.

(21) Appl. No.: 12/052,383

(22) Filed: Mar. 20, 2008

(65) Prior Publication Data

US 2008/0281075 A1 Nov. 13, 2008

Related U.S. Application Data

(63) Continuation-in-part of application No. 12/066,727, filed as application No. PCT/GB2005/003797 on Sep. 30, 2005, now abandoned.

(30) Foreign Application Priority Data

Sep. 13, 2005 (GB) .................................. 0518667.1

(51) Int. Cl.
*C07K 1/02* (2006.01)
*C07K 1/00* (2006.01)
*C07K 5/00* (2006.01)
(52) U.S. Cl. ......................... 530/317; 530/333; 530/338
(58) Field of Classification Search ........................ None
See application file for complete search history.

(56) References Cited

U.S. PATENT DOCUMENTS

| 4,251,438 | A | 2/1981 | Moon |
| 6,294,539 | B1 | 9/2001 | Lou et al. |

FOREIGN PATENT DOCUMENTS

WO 9517418 A2 6/1995

OTHER PUBLICATIONS

Dellaria, et al., "Enantioselective Synthesis of α-Amino Acid Derivatives via the Stereoselective Alkylation of a Homochiral Glycine Enolate Synthon", J. Org. Chem., 1989, 54, 3916-3926.
Kashima, et al., "Nucleophilic Ring-Opening Reactions of Morpholin-2-ones. A Resolution of *d*1-(Secondary-alkyl)amines" J. Org. Chem., 1989, 54, 789-792.
Lee, et al., "Asymmetric Synthesis and Epimerization of Aryloxazinones", Bull. Korean Chem. Soc., 1999, 20:3, 264-266.
Dorow, R.L., et al., "A Novel, One-Pot Preparation of N-Methyl-α-Amino Acid Dipeptides from Oxazolidinones and Amino Acids," Tetrahedron Letters, 40: 467-470 (1999).
Shrader, W.D., et al., "A Short Asymmetric Synthesis of N-α-FMOC-N-δ-BOC-α-Methyl-D-Ornithine," Bioorganic & Medicinal Chemistry Letters, 5(19): 2207-2210 (1995).
Zhang, Y., et al., "A Facile Synthesis of L-analyl-peptides from 5-Oxazolidinone," Hecheng Huaxue, pp. 125-127 (1999).
Pyne, Stephen G., et al., "Diastereoselective Addition of α-Hydroxyalkyl and α-Alkoxyalkyl Radicals to Chiral 4-Methyleneoxazolidin-5-ones," Tetrahedron, 54: 5709-5720 (1998).
Seebach, D., et al., "N,O-Acetals from Pivalaldehyde and Amino Acids for the α-Alkylation with Self-Reproduction of the Center of Chirality. Enolates of 3-Benzoyl-2-(tert-butyl)-1,3-oxazolidin-5-ones," Helvetica Chimica Acta, 68: 1243:1250 (1985).
Kogan, T., et al., "The Synthesis of Chiral 3-Oxo-6-[(phenylmethoxy)carbonyl]-2-piperazineacetic Acid Esters Designed for the Presentation of an Aspartic Acid Side Chain. A Subsequent Novel Friedel Crafts Reaction," Tetrahedron Letters, 33(47): 7089-7092 (1992).
Chen, et al., "Bioactive Pseudopeptidic Analogues and Cyclostereoisomers of Osteogenic Growth Peptide C-Terminal Pentapeptide, OGP(10-14)", Journal of Medicinal Chemistry, Apr. 11, 2002, vol. 45, No. 8, pp. 1624-1632 XP002599698 ISSN: 0022-2623.
Le, et al., "Bioactive Peptidic Analogues and Cyclostereoisomers of the Minimal Antinociceptive Histogranin Fragment-(7-10)", Journal of Medicinal Chemistry, Jul. 3, 2003, vol. 46, No. 14, pp. 3094-3101 XP002599699 ISSN: 0022-2623.
Tchertchian, et al., "Synthesis of $N^\alpha$-(1-Phenyl-2-mercaptoethyl) Amino Acids, New Building Blocks for Ligation and Cyclization at Non-Cysteine Sites: Scope and Limitations in Peptide Synthesis", Journal of Organic Chemistry, Dec. 24, 2004, vol. 69, No. 26, pp. 9208-9214 XP002599697 ISSN: 0022-3263.

*Primary Examiner* — Julie Ha
(74) *Attorney, Agent, or Firm* — Stoel Rives LLP

(57) ABSTRACT

A process comprising substitution of an acceptor molecule comprising a group —XC(O)— wherein X is O, S, or $NR^8$, where $R^8$ is $C_{1-6}$ alkyl, $C_{6-12}$ aryl or hydrogen, with a nucleophile, wherein the acceptor molecule is cyclised such that said nucleophilic substitution at —XC(O)— occurs without racemisation, is provided. This process has particular application for the production of a peptide by extension from the activated carboxy-terminus of an acyl amino acid residue without epimerisation.

11 Claims, No Drawings

ASYMMETRIC SYNTHESIS OF PEPTIDES

RELATED APPLICATION

This application is a continuation-in-part of U.S. application Ser. No. 12/066,727, filed Mar. 13, 2008, which is the U.S. national stage of International Application No. PCT/GB05/03797, which designated the United States and was filed on Sep. 30, 2005, published in English, which claims priority under 35 U.S.C. §119 or 365 to United Kingdom, Application No. 0518667.1, filed 13 Sep. 2005. The entire teachings of the above applications are incorporated herein by reference.

BACKGROUND OF THE INVENTION

The present invention relates to a novel process for peptide synthesis, by the addition of amino acids to the activated C-terminus of a peptide chain. Peptide synthesis is central to the manufacture of many drugs and medicaments. Peptides or derivatives thereof are used for the treatment of many disorders from antibiotics to anticancer agents. Therefore improving peptide synthesis and the yield of peptide produced by chemical synthesis has been the focus of much research in recent years.

Chemical synthesis of proteins or peptides has been a particular focus in the art. The chemical synthesis of proteins or peptides allows the production of purified peptides of specific amino acid sequence. It also allows the production of truncated sequences of amino acids and allows the introduction of non-natural amino acid derivatives.

Proteins are produced in nature by the stepwise condensation of amino acid monomers on a ribosome. Synthesis of the protein begins from the N-terminal residue and grows towards the C-terminus. The conventional approach to peptide synthesis has concentrated on extension at the N-terminus of a growing peptide. This approach forms the basis of conventional solid phase peptide synthesis. Peptide synthesis solely by extension from the N-terminus is limiting as it renders any peptide synthesis lineal in nature, rather than convergent. This can severely increase overall length of synthesis, increase operational time and decrease overall yield with consequent possibilities for the loss of stereochemical fidelity.

To overcome the problems associated with N-terminal extension of a peptide, it could be envisaged that the synthesis could instead provide extension of a peptide from the C-terminal. However, attempts at peptide synthesis in the N to C direction have been generally unsuccessful due to epimerisation of the carboxy-terminal amino acid residue. This is due to the tendency of carboxy-terminal-activated acylamino acids and peptides to form oxazolones. As illustrated below, the formation of the oxazolone allows rapid racemisation of the alpha-position of the terminal amino acid residue of the acyl amino acid or peptide.

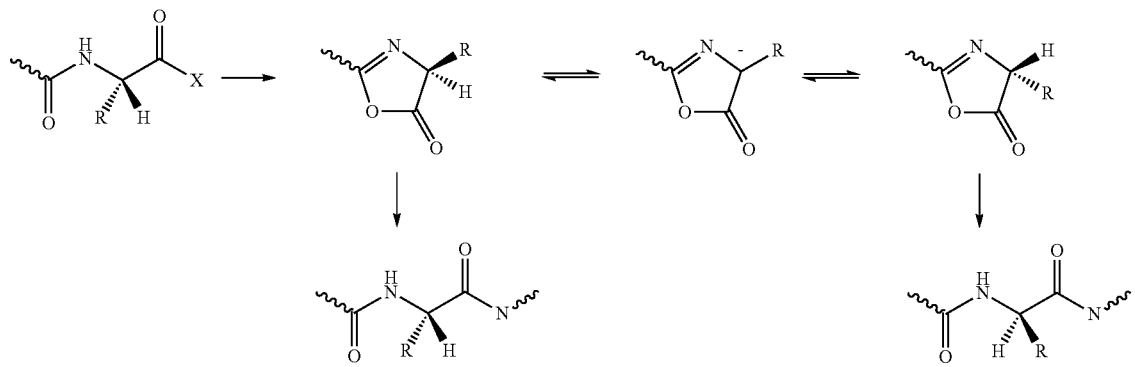

This racemisation prevents the production of stereochemically homogeneous peptides by C-terminus extension.

It will be appreciated that the production of isomerically pure compounds is a particular requirement in the art. Any method which results in the production of a mixture of isomers will require the use of time consuming and expensive purification steps to separate the isomers. Chiral compounds which are administered to humans or animals are usually required in enantiomerically pure form. The presence of unwanted isomers even in low concentrations can reduce the potency of the compound and can produce unwanted and in some cases disastrous side effects. The incorporation of an unwanted enantiomer into a peptide chain (for example the incorporation of a D-amino acid into a peptide composed of L-amino acids) may disrupt the folding and/or 3D shape of the peptide, thus resulting in a peptide which may have unpredictable binding activities and/or biological properties. The production of enantiomerically pure peptides is therefore of paramount importance.

Various attempts have been made to overcome this problem. Iorga, B and Campagne, J-M (2004, Synlett 10, 1826-1828) attempted to reduce the degree of epimerisation by improving the rate of peptide bond formation over the rate of oxazolone formation so that peptide bond formation was the predominant reaction. However, this method does not entirely prevent the formation of the oxazolone and therefore epimerisation at the carboxy-terminal activated amino acid residue occurs. Native chemical ligation has been developed to overcome problems of carboxy-terminal extension but is ordinarily restricted to couplings in which the amino-terminal partner is an assisting cysteine residue and is not applicable to general techniques of automated solid phase peptide synthesis. The application of native chemical ligation to other amino-terminal amino acids has had very limited success.

The present invention provides a new method of producing a peptide by extension from the activated carboxy-terminus of an acyl amino acid residue. This new method overcomes the problems of epimerisation of the terminal amino acid residue during the coupling step. The present invention therefore allows the production of peptides by a convergent approach and provides a new method for the production of potentially biologically important compounds instead of the linear repetitive amino terminal extension approach currently used.

The first aspect of the present invention provides a process comprising substitution of an acceptor molecule comprising a group —XC(X)— (preferably —X(CO)—) wherein each X is independently O, S or $NR^8$, where $R^8$ is hydrogen, aliphatic group or an aromatic group, preferably hydrogen, $C_{1-6}$ alkyl, $C_{6-12}$ aryl, with a nucleophile, wherein the acceptor molecule is cyclised such that said nucleophilic substitution at —XC(X)— occurs without racemisation. The acceptor molecule is preferably a cyclised amino acid or derivative thereof. In particular, the acceptor molecule is a compound of formula (II):

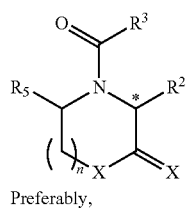

Preferably,

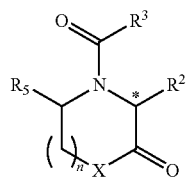

wherein each X is O, S, or $NR^8$, where $R^8$ is as defined above; $R^2$ is independently selected from an aliphatic group, such as a $C_{1-10}$ branched or straight chain alkyl group, or an aromatic group, such as $C_{5-12}$ heteroaryl group or $C_{6-12}$ aryl group, each optionally substituted with a group including, for example, $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$;
$R^3$ is as defined for $R^2$ or is hydrogen, or a group

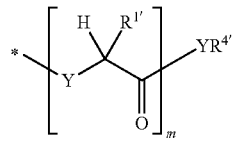

or a group

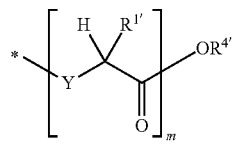

a group —$C(R^{1'})(R^9)$—$N(R^{10})(R^{11})$;
wherein $R^{1'}$ is independently selected from an aliphatic group such as $C_{1-10}$ branched or straight chain alkyl group, an aromatic, such as $C_{5-12}$ heteroaryl group or $C_{6-12}$ aryl group, each optionally substituted with a group such as $OR^{13}SR^{13}$, $N(R^{13})_2$, $CO_2R^{13}$, $CON(R^{13})_2$, $SO_2R^{12}$, $SO_3R^{12}$, phenyl, imidazolyl indolyl, hydroxyphenyl or $NR^{13}C(=NR^{13})N(R^{13})_2$;
wherein when Y is $NR^8$, $R^8$ and $R^{1'}$ can together form a 4 to 7 membered ring, optionally substituted with a group such as $CO_2R^{13}$, $OR^{13}$, $SR^{13}$, $N(R^{13})_2$, $CO_2R^{13}$, $CON(R^{13})_2$, $C_{1-10}$ alkyl or $C_{6-12}$ aryl, wherein said ring can be fully, partially or unsaturated, and wherein the ring may contain one or more additional heteroatoms selected from O, S or N;
$R^{12}$ is hydrogen, $C_{1-6}$ alkyl $C_{6-12}$ aryl or $N(R^{13})_2$, wherein each occurrence of $R^{13}$ is independently hydrogen, $C_{1-6}$ alkyl or $C_{6-12}$ aryl, and $R^{4'}$ is a carboxyl protecting group or hydrogen;
$R^9$ and $R^{10}$ are independently hydrogen or a group as defined for $R^{1'}$;
$R^{11}$ is hydrogen or an amino protecting group preferably selected from a benzyloxycarbonyl group, a t-butoxycarbonyl group, a 2-(4-biphenylyl)-isopropoxycarbonyl group, a fluorenylmethoxycarbonyl group, a triphenylmethyl group and/or a 2-nitrophenylsulphenyl group;
or $R^9$ and $R^{10}$ or $R^{10}$ and $R^{11}$ or $R^{1'}$ and $R^{10}$ or two $R^{13}$ can together form a 4 to 7 membered ring, optionally substituted with a group such as $CO_2R^{13}$, $OR^{13}$, $SR^{13}$, $N(R^{13})_2$, $CO_2R^{13}$, $CON(R^{13})_2$, $C_{1-10}$ alkyl or $C_{6-12}$ aryl, wherein said ring can be fully, partially or unsaturated, and wherein the ring may contain one or more additional heteroatoms selected from O, S or N;
Y is O, S or $NR^8$, where $R^8$ is as defined above;
$YR^{4'}$ is $R^3$;
$R^5$ is an aromatic group such as $C_{6-12}$ aryl, $C_{5-12}$ heteroalkyl or an aliphatic group such as $C_{1-8}$ branched or straight chain alkyl optionally substituted with a group such as $OR^{13}$, $SR^{13}$, $N(R^{13})_2$, $CO_2R^{13}$, $CON(R^{13})_2$, phenyl, imidazolyl, indolyl, hydroxyphenyl or $NR^{13}C(=NR^{13})N(R^{13})_2$ or a linker for attachment of formula (II) to a resin or a linked resin;
n is 0, 1, 2 or 3 and m is an integer, such as an integer selected from 1-100.

The nucleophilic substitution of the acceptor molecule preferably occurs without epimerisation.

Preferably, the process is carboxy terminal extension of an acceptor molecule, for example an amino acid or peptide. The invention therefore provides a process for the synthesis of a peptide or a peptide analog by carboxy terminal extension, by the addition of a nucleophile to an acceptor molecule such as a compound of formula (II).

There is further provided a process for the production of a compound of formula (I)

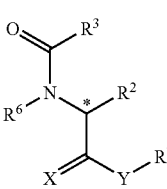

comprising reaction of a compound of formula (II) or (II') (above)
with a compound of formula (III)

wherein the variables are defined as above:
preferably X is O, S, or $NR^8$, where $R^8$ is as defined above, Y is O, S or NH;

$R^2$ is independently selected from a $C_{1-10}$ branched or straight chain alkyl group, $C_{5-12}$ heteroaryl group or $C_{6-12}$ aryl group, optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$;

$R^3$ is as defined for $R^2$ or is hydrogen, or a group

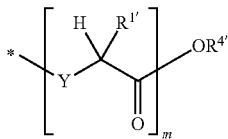

or a group $-C(R^{1'})(R^9)-N(R^{10})(R^{11})$;

wherein $R^{1'}$ is hydrogen or as defined from $R^1$ below; Y is as defined above and $R^{4'}$ is as defined for $R^4$ below;

$R^{12}$ is hydrogen, $C_{1-6}$ alkyl, $C_{6-12}$ aryl or $N(R^{13})_2$, wherein each occurrence of $R^{13}$ is independently hydrogen, $C_{1-6}$ alkyl or $C_{6-12}$ aryl, $R^9$ and $R^{10}$ are independently hydrogen or a group as defined for $R^{1'}$;

or $R^9$ and $R^{10}$ can together form a 4 to 7 membered ring, optionally substituted with $CO_2R^{13}$, $OR^{13}$, $SR^{13}$, $N(R^{13})_2$, $CO_2R^{13}$, $CON(R^{13})_2$, $C_{1-10}$ alkyl or $C_{6-12}$ aryl, wherein said ring can be fully, partially or unsaturated, and wherein the ring may contain one or more additional heteroatoms selected from O, S or N, $R^{11}$ is hydrogen or an amino protecting group preferably selected from a benzyloxycarbonyl group, a t-butoxycarbonyl group, a 2-(4-biphenylyl)-isopropoxycarbonyl group, a fluorenylmethoxycarbonyl group, a triphenylmethyl group and/or a 2-nitrophenylsulphenyl group;

$R^5$ is an aromatic group, such as $C_{5-12}$ aryl, $C_{5-12}$ heteroalkyl or an aliphatic group, such as $C_{1-8}$ branched or straight chain alkyl optionally substituted with $OR^{13}$, $SR^{13}$, $N(R^{13})_2$, $CO_2R^{13}$, $CO N(R^{13})_2$, phenyl, imidazolyl, indolyl, hydroxyphenyl or $NR^{13}C(=NR^{13})N(R^{13})_2$ or a linker for attachment of formula (II) to a resin or a linked resin; $R^6$ is hydrogen or

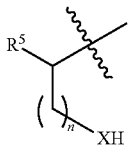

wherein $R^5$ and X are as defined above;

$R^7$ is a chiral, substituted methylene, such as a group

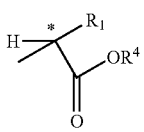

or is independently selected from an aliphatic group such as a $C_{1-10}$ branched or straight chain alkyl group or an aromatic group, such as a $C_{6-12}$ aryl group, optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$);

or wherein $R^7$ and Y together form a 4 to 7 membered ring, optionally substituted with a group such as $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$, wherein said ring can be fully, partially or unsaturated, and wherein the ring may contain one or more heteroatoms in addition to Y, selected from O, S or N;

wherein $R^1$ is $R^{1'}$ or is independently selected from an aliphatic group such as $C_{1-10}$ branched or straight chain alkyl group, or an aromatic group such as $C_{5-12}$ heteroaryl group or $C_{6-12}$ aryl group optionally substituted with a group such as $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$;

and $R^4$ is $R^{4'}$ or a carboxyl protecting group or hydrogen; n is 0, 1, 2 or 3 and m is an integer such as a value selected from 1-100 and when n=0, $R^6$ is H.

The inventors have surprisingly found that activation of an amino acid or peptide via a cyclic compound as exemplified in formula (II) prevents the formation of an oxazolone thereby allowing the condensation of a compound of formula (III) without concomitant epimerisation. The invention therefore provides peptides via C-terminus extension, said peptides being produced in an enantiomerically and diastereochemically pure form.

The use of activated cyclic N-acyl amino acids, peptides or derivatives thereof eliminates oxazolone formation and associated epimerisation. The use of cyclic activated intermediates in the present invention provides an improved method of peptide synthesis via carboxy-terminal extension.

Therefore, rather than merely reducing the probability of epimerisation occurring, as has been attempted in the prior art, the process of the present invention does not permit epimerisation and therefore guarantees the production of a peptide of correct stereochemistry as the activated carboxyl terminus is held in a cyclic template such that the adjacent amide cannot form the oxazolone.

In accordance with usual practice, * denotes a stereocenter (asymmetric center). Where a compound contains a stereocenter (whether marked in the present application with * or not) the stereochemistry of the asymmetric centers may be in the R or S configuration. The compounds of the present application can be provided in enantiomerically pure form or as a mixture of isomers (including a racemic mixture). Preferably, the compounds of the present inventions are provided in an enantiomerically pure form. The present invention allows maintenance of the desired stereochemistry throughout the synthetic pathway. Thus wherein Y is NH, the amino acids to be attached may be of L or D configuration as required.

Preferably $R^1$ and $R^2$ are independently selected from $C_{1-4}$ branched or straight chain alkyl optionally substituted with $OR^{13}$, $SR^{13}$, $N(R^{13})_2$, $CO_2R^{13}$, $CON(R^{13})_2$, phenyl, imidazolyl, indolyl, hydroxyphenyl or $NR^{13}C(=NR^{13})N(R^{13})_2$, preferably optionally substituted with OH, SH, $NH_2$, $CO_2H$, $CONH_2$, phenyl, imidazolyl, indolyl, hydroxyphenyl or $NH(C=NH)NH_2$.

More preferably, R and R are independently selected from $C_1$ alkyl optionally substituted with OH, SH, $CO_2H$, $CONH_2$, phenyl, imidazolyl, indolyl or hydroxyphenyl; $C_2$ alkyl optionally substituted with OH, $CO_2H$, $CONH_2$ or $SCH_3$; $C_3$ alkyl optionally substituted with $NHC(=NH)NH_2$ or $C_4$ alkyl optionally substituted with $NH_2$.

The integer, m is preferably 1-50, more preferably 1 to 30, most preferably 1, 2, 3, 4, 5, 6, 7, 8, 9, 10, 11, 12, 13, 14, 15, 16, 17, 18, 19 or 20. The integer n is preferably 0 or 1.

When X is NR, R is preferably $C_{1-4}$ alkyl more preferably methyl, ethyl, n-propyl, iso-propyl, n-butyl or tert-butyl, phenyl, naphthyl, anthracenyl or phenanthracenyl, more preferably phenyl or hydrogen.

$R^3$ may also be substituted pipecolic acid or derivative thereof, α-alkoxy-α-amino acids, α,α-diamino acids, β-substituted dehydroamino acids, canavanine, cysteinesulphonamide, homocysteinesulphonamide, γ,δ-unsaturated amino acids, substituted 4-hydroxyprolines, 4-hydroxtyornlithines, imino sugars, Fmoc-BPC—OH, Fmoc-TPG-OH and Fmoc-CAA-OH, or (5)-3,5-dihydroxyphenylglycine.

It will be appreciated by a person skilled in the art that amino acids, hydroxy acids and derivatives thereof contain functional groups which require protection. In particular it is known in the art to protect the amino terminus, the carboxyl terminus and/or the side chains of an amino acid or peptide (for example wherein $R^1$ or $R^2$ is $CH_2CO_2H$ or $CH_2CH_2OH$). Examples of such protection are well known in the art. In particular the amino terminus of an amino acid may be protected by one or more of a benzyloxycarbonyl group, a t-butoxycarbonyl group, a 2-(4-biphenylyl)-isopropoxycarbonyl group, a fluorenylmethoxycarbonyl group, a triphenylmethyl group and/or a 2-nitrophenylsulphenyl group. The carboxyl group can be protected by one or more of an ester group especially a methyl, ethyl, benzyl, t-butyl or phenyl ester. Thus $R^4$ is preferably methyl, ethyl, benzyl, t-butyl or phenyl.

Conditions for the removal of the protecting groups discussed above are well known in the art. The protecting groups may be removed after each coupling reaction (for example, the carboxyl protection) or alternatively at the end of the synthesis (for example, the side chain protection and/or the N-terminal group).

In a particular feature of the first aspect, the invention provides a process for production of a compound of formula (Ia)

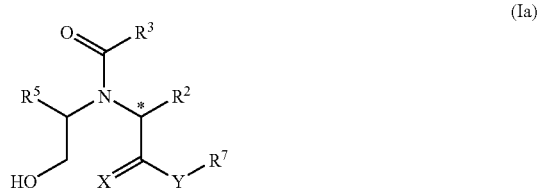

(Ia)

comprising reacting a compound of formula (IIa) (above) with a compound of formula (III) HY—$R^7$;
Wherein the groups Y, X, $R^2$, $R^3$, $R^5$, and $R^7$ are as defined above.
In an alternative feature of the first aspect, the invention provides a process for production of a compound of formula (Ib)

(Ib)

comprising reacting a compound of formula (IIb)

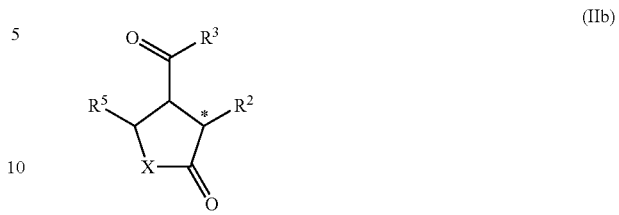

(IIb)

with a compound of formula (III) HY—$R^7$
wherein the groups Y, X, $R^2$, $R^3$, $R^5$ and $R^7$ are as defined above for compounds (I), (II) and (III).

The N and the terminal ester of formula (I), (Ia) or (Ib) can be unmasked by processes known in the art, for example, sodium liquid ammonia in the presence of an alcohol when $R^1$=phenyl and $R^4$=t-butyl. Alternatively, the ester can be further derivatized, including for example, amidation.

The nucleophilic substitution of the acceptor molecule of the first aspect of the invention can be carried out using reaction conditions known in the art. In some circumstances, for example where the nucleophile and/or the acceptor molecule are sterically hindered it may be necessary for example to use high pressure such as around 19-20 bar, and/or longer reaction times such as 12-72 hours, preferably 24-48 hours. Alternatively, the reaction can be carried out in the presence of a reagent such as $AlMe_3$. When the substitution is carried out on the solid phase, the reaction can be promoted by the use of an excess of nucleophile.

The invention further relates to a process for the production of a compound of formula (II) (above) by the reaction of a compound of formula (IV)

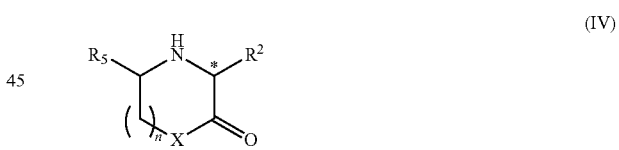

(IV)

with a compound of formula (V) Z—CO—$R^3$ wherein Z is any substituent capable of being involved in peptide bond formation preferably hydroxide, halide or azide, and $R^2$, $R^3$, $R^5$, X and n are as defined above. It will be appreciated that when $R^3$ is a protected peptide, subsequent N-terminus extension may be carried out using peptide synthesis methods known in the art, such as deprotection and further peptide bond formation.

The process of the present invention can particularly be used for the production of cyclic compounds, for example cyclic peptides.

It will be appreciated that when $R^3$ is $C(R^{1'})(R^9)$—$N(R^{10})(R^{11})$, the compound of formula (II) can be reacted with one or more compounds of formula (V) in a stepwise direction.

The present invention therefore encompasses a compound of formula (VII);

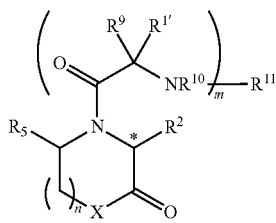

(VII)

wherein the variables are described above, preferably m is an integer of 1 to 50, preferably 1 to 30, more preferably 1, 2, 3, 4, 5, 6, 7, 8, 9, 10, 11, 12, 13, 14, 15, 16, 17, 18, 19 or 20; and $R^{1'}$, $R^2$, $R^5$, $R^9$, $R^{10}$, $R^{11}$, X and n are as defined above.

The compound of formula (VII) can be used in a process for the formation of a compound of formula (I) (illustrated below as (Ic));

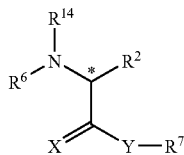

(Ic)

when $R^{14}$ is —[C(O)—C($R^9$)($R^{1'}$)—N($R^{10}$)—]$_m$—($R^{11}$) and $R^{1'}$, $R^2$, $R^6$, $R^7$, $R^9$, $R^{10}$, $R^{11}$, m, X and Y are as described above, comprising, reaction of a compound of formula (VII) with a compound of formula (III) as described above. The compound of formula (I) can then be converted into a compound of formula (VI) by removal of the group $R^6$ as described below. For the compound of formula (VII) and compounds of formula (I) or (VI) obtained therefrom, the substituents $R^1$ and $R^9$ can be replaced by a group (=$R^1$) wherein $R^1$ is as described above.

It will be appreciated that when m is 3 or more, and $R^{10}$ and $R^{11}$ are hydrogen, condensation can occur at the X—C(O)— functionality of the compound of formula (VII) to form a cyclised compound of formula (VIII);

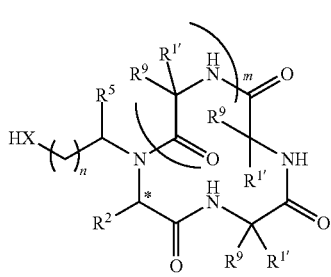

(VIII)

wherein the variables are as defined above.

The present invention therefore provides a compound of formula (VIII). In addition, the invention provides a process for the production of a compound of formula (VIII) comprising cyclisation of a compound of formula (VII) wherein m is 3 or more. Reaction of the compound of formula (VIII) under reducing conditions (for example in the presence of lithium and liquid ammonia) results in the formation of a compound of formula (IX);

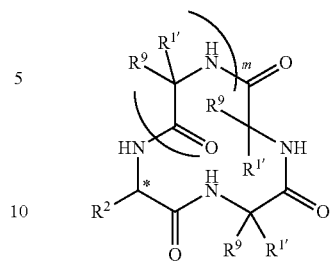

(IX)

wherein $R^{1'}$, $R^2$, $R^9$, X and m are as defined above.

The present invention therefore provides a compound of formula (IX) and a process for the production of a compound of formula (IX) comprising the reduction of a compound of formula (VIII).

It will be appreciated that the process of the present invention can be carried out in solution. Alternatively, a compound of formula II may be attached to a resin via the group $R^5$ and the peptide synthesis carried out via solid phase peptide synthesis. When $R^5$ is a linker it can be a group $OR^{13}$, $N(R^{13})_2$, $CO_2R^{13}$ or $SR^{13}$, or an alkyl group having 1 to 4 carbons or a $C_{6-12}$ aryl group, said alkyl and aryl groups being optionally substituted with $OR^{13}$, $N(R^{13})_2$, $CO_2R^{13}$ or $SR^{13}$. Alternatively, part of the synthesis may be carried out on the solid phase and part in solution.

The compound of formula II can be attached to and removed from a resin using methods known in the art.

Solid phase peptide synthesis using the process of the present invention may be carried out by using procedures attaching the carboxy-terminal to any resin known in the art. Examples of suitable resins include Wang, Merrifield, polyamide, 2-chlorotrityl, Rink, Knorr, DCHD, PAL and any other known in the art. Solid phase coupling partners such as BOP, PyBOP) and DCC may be used, as well as any other suitable coupling partners known in the art.

A further feature of the first aspect is a process for the production of a compound of formula (VI)

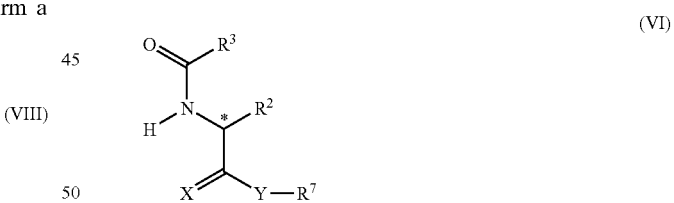

(VI)

from formula (I)

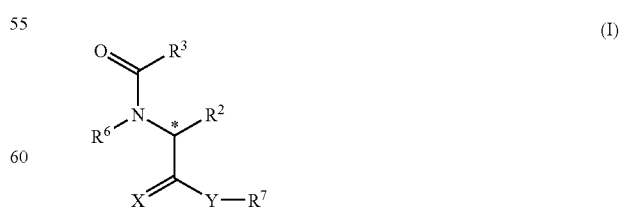

(I)

by the removal of $R^6$ by any method known in the art, wherein X, Y, $R^2$, $R^3$, $R^6$ and $R^7$ are as defined above. It will be appreciated that when $R^6$ is hydrogen, the compound of formula (I) corresponds to the compound of formula (VI).

In particular, the removal of the group $R^6$ may be carried out under reducing conditions such as under Birch conditions (i.e. with lithium and liquid ammonia). As it will be appreciated by the skilled person, the peptide produced by the process of the first aspect may be post modified by any suitable method known in the art. A second aspect of the present invention relates to the compounds described herein, including a compound of formula (II)

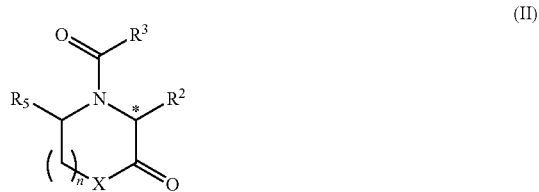

wherein X is O, S or $NR^8$, where $R^8$ is $C_{1-6}$ alkyl $C_{6-12}$ aryl or hydrogen $R^2$ is independently selected from a $C_{1-10}$ branched or straight chain alkyl group, $C_{5-12}$ heteroaryl group or $C_{6-12}$ aryl group, optionally substituted with $OR^{13}$, $SR^{13}N(R^{13})_2$, $CO_2R^{13}$, $CON(R^{13})_2$, $SO_2R^{12}$, $SO_3R^{12}$ phenyl, imidazolyl, indolyl, hydroxyphenyl or $NR^{13}C(=NR^{13})N(R^{13})_2$; $R^3$ is as defined for $R^2$ or is hydrogen, or a group

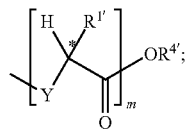

or a group $—C(R^{1'})(R^9)—N(R^{10})(R^{11})$ wherein $R^1$ is independently selected from a $C_{1-10}$ branched or straight chain alkyl group, $C_{5-12}$ heteroaryl group or $C_{6-12}$ aryl group optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$ wherein when Y is $NR^8$, $R^8$ and $R^{1'}$ can together form a 4 to 7 membered ring, optionally substituted with $CO_2R^{13}$, $OR^{13}$, $SR^{13}$, $N(R^{13})_2$, $CO_2R^{13}$, $CON(R^{13})_2$, $C_{1-10}$ alkyl or $C_{6-12}$ aryl, wherein said ring can be fully, partially or unsaturated,
and wherein the ring may contain one or more heteroatoms selected from O, S or N; $R^{12}$ is hydrogen, $C_{1-6}$ alkyl, $C_{6-12}$ aryl or $N(R^{13})_2$, wherein each occurrence of $R^{13}$ is independently hydrogen, $C_{1-6}$ alkyl or $C_{6-12}$ aryl, $R^9$ and $R^{10}$ are independently hydrogen or a group as defined for $R^1$; or $R^9$ and $R^{10}$ can together form a 4 to 7 membered ring, optionally substituted with $CO_2R^{13}$, $OR^{13}$, $SR^{13}$, $N(R^{13})_2$, $CO_2R^{13}$, $CON(R^{13})_2$, $C_{1-10}$ alkyl or $C_{6-12}$ aryl, wherein said ring can be fully, partially or unsaturated, and wherein the ring may contain one or more heteroatoms selected from O, S or $NR^{11}$ is hydrogen or an amino protecting group preferably selected from a benzyloxycarbonyl group, a t-butoxycarbonyl group, a 2-(4-biphenylyl)-isopropoxycarbonyl group, a fluorenylmethoxycarbonyl group, a triphenylmethyl group and/or a 2-nitrophenylsulphenyl group; $R^1$ is independently selected from $C_{1-10}$ branched or straight chain alkyl optionally substituted with $OR^{13}$, $SR^{13}$, $N(R^{13})_2$, $CO_2R^{13}$, $CO\,N(R^{13})_2$, phenyl, imidazoyl, indolyl, hydroxyphenyl or $NR^{13}C(=NR^{13})N(R^{13})_3$ and $R^{4'}$ is a carboxyl protecting group or hydrogen and n is 0, 1, 2 or 3, m is 1-100; and $R^5$ is a linker for attachment of formula (II) to a resin, a linked resin, or $C_{6-12}$ aryl, $C_{5-12}$ heteroalkyl or $C_{1-8}$ branched or straight chain alkyl optionally substituted with $OR^{13}$, $SR^{13}$, $N(R^{13})_2$, $CO_2R^{13}$, $CON(R^{13})_2$, phenyl, imidazolyl, indolyl, hydroxyphenyl or $NR^{13}C(=NR^{13})N(R^{13})_2$; wherein when X=O, and $R^5$ is phenyl, n is not 0 or 1.

Preferably $R^1$ and $R^2$ are independently selected from $C_{1-4}$ branched or straight chain alkyl optionally substituted with $OR^{13}$, $SR^{13}$, $N(R^{13})_2$, $CO_2R^{13}$, $CON(R^{13})_2$, phenyl, imidazolyl, indolyl, hydroxyphenyl or $NR^{13}C(=NR^{13})N(R^{13})_2$. More preferably $R^1$ and $R^2$ are independently selected from $C_1$ alkyl optionally substituted with $OR^{13}$, $SR^{13}$, $CO_2R^{13}$, $CO\,N(R^{13})_2$, phenyl, imidazolyl, indolyl or hydroxyphenyl; $C_2$ alkyl optionally substituted with $OR^{13}$, $CO_2R^{13}$, $CON(R^{13})_2$ or $SCH_3$; $C_3$ alkyl $NR^{13}C(=NR^{13})N(R^{13})_2$ or $C_4$ alkyl optionally substituted with $N(R^{13})_2$.

As set out above, $R^4$ is a carboxyl protecting group, such as an ester group. In particular $R^4$ is preferably methyl, ethyl, benzyl, t-butyl or phenyl. When $R^5$ is a linker it can be $OR^{13}$, $N(R^{13})_2$, $CO_2R^{13}$ or $SR^{13}$ or an alkyl group having 1 to 4 carbons or a $C_{6-12}$ aryl group, wherein the alkyl group and/or aryl group can be substituted with one or more of $OR^{13}$, $N(R^{13})_2$, $CO_2R^{13}$ or $SR^{13}$.

The integer, m is preferably 1-50, more preferably 1 to 30, most preferably 1, 2, 3, 4, 5, 6, 7, 8, 9, 10, 11, 12, 13, 14, 15, 16, 17, 18, 19 or 20. The integer n is preferably 0 or 1.

When X is $NR^8$, $R^8$ is preferably $C_{1-4}$ alkyl, more preferably methyl, ethyl, n-propyl, iso-propyl, n-butyl or tert-butyl, phenyl, naphthyl, anthracenyl or phenanthracenyl, more preferably phenyl or hydrogen.

$R^{13}$ is preferably hydrogen or $C_{1-4}$ alkyl, more preferably methyl, ethyl, n-propyl, iso-propyl, n-butyl or tert-butyl.

For the purposes of this invention, alkyl relates to both straight chain and branched, saturated or unsaturated alkyl radicals having, for example, 1 to 10 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. Alkyl therefore relates to a group having 1, 2, 3, 4, 5, 6, 7, 8, 9 or 10 or more carbon atoms. The term alkyl also encompasses cycloalkyl radicals of 3 to 12 carbon atoms, preferably 4 to 8 carbon atoms, and most preferably 5 to 6 carbon atoms including, but not limited to cyclopropyl, cyclobutyl, $CH_2$-cyclopropyl, $CH_2$-cyclobutyl, cyclopentyl or cyclohexyl. Cycloalkyl groups may be optionally substituted or fused to one or more carbocyclyl or heterocyclyl group. Haloalkyl relates to an alkyl radical preferably having 1 to 8 carbon atoms, preferably 1 to 4 carbon atoms substituted with one or more halide atoms for example $CH_2CH_2Br$, $CF_3$ or $CCl_3$. An alkyl group may be optionally interrupted by one or more O, S or NH groups, preferably one or more O atoms to form an alkoxy group. An alkyl group may be optionally interrupted by one or more double or triple bonds to form a group including but not limited to ethylene, n-propyl-1-ene, n-propyl-2-ene, isopropylene, ethynyl, 2-methylethynyl etc.

"Aryl" means an aromatic 6 to 12 membered hydrocarbon or heteroaryl containing one ring or being fused to one or more saturated or unsaturated rings including but not limited to phenyl, naphthyl, anthracenyl or phenanthracenyl. "Heteroaryl" means an aromatic 5 to 12 membered aryl containing one or more heteroatoms selected from N, O or S and containing one ring or being fused to one or more saturated or unsaturated rings including but not limited to furan, imidazole, indole, oxazole, purine, pyran, pyridine, pyrimidine, pyrrole, tetrahydrofuran, thiophene and triazole. The aryl and heteroaryl groups can be fully saturated, partially saturated or unsaturated.

Halogen means F, Cl, Br or I, preferably F.

A third aspect of the invention relates to the use of a compound of formula (II) as defined in the first and/or second aspects of the invention in asymmetric synthesis.

All preferred features of each of the aspects of the invention apply to all other aspects mutatis mutandis.

The present invention will now be illustrated by reference to one or more of the following non-limiting examples:

EXAMPLES

Example of a method for the production of a cyclic peptide.

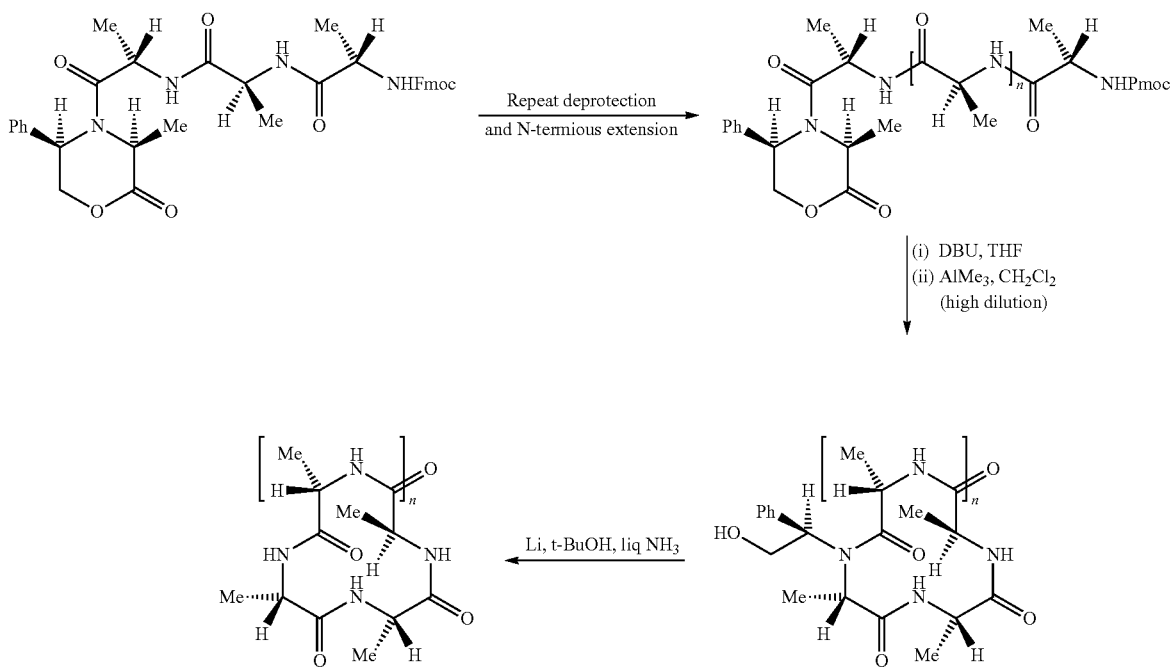

Example of a method for N-terminal extension of a compound of formula (II).

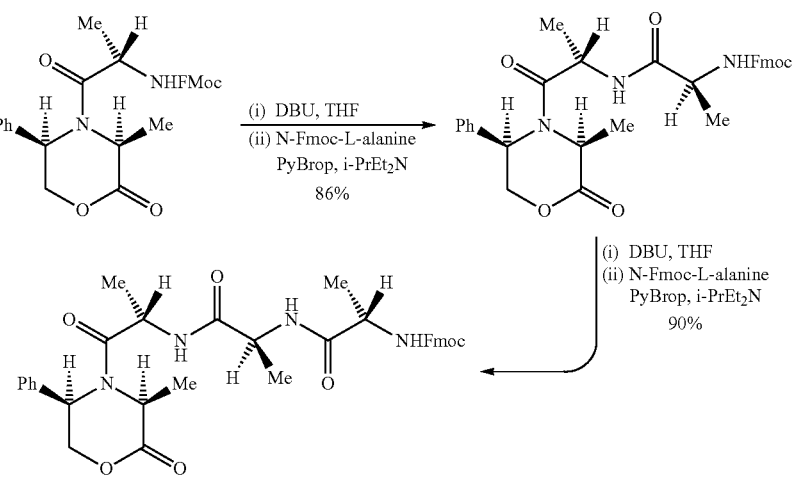

Example of a method for use of the compound of formula (II) in solid phase synthesis

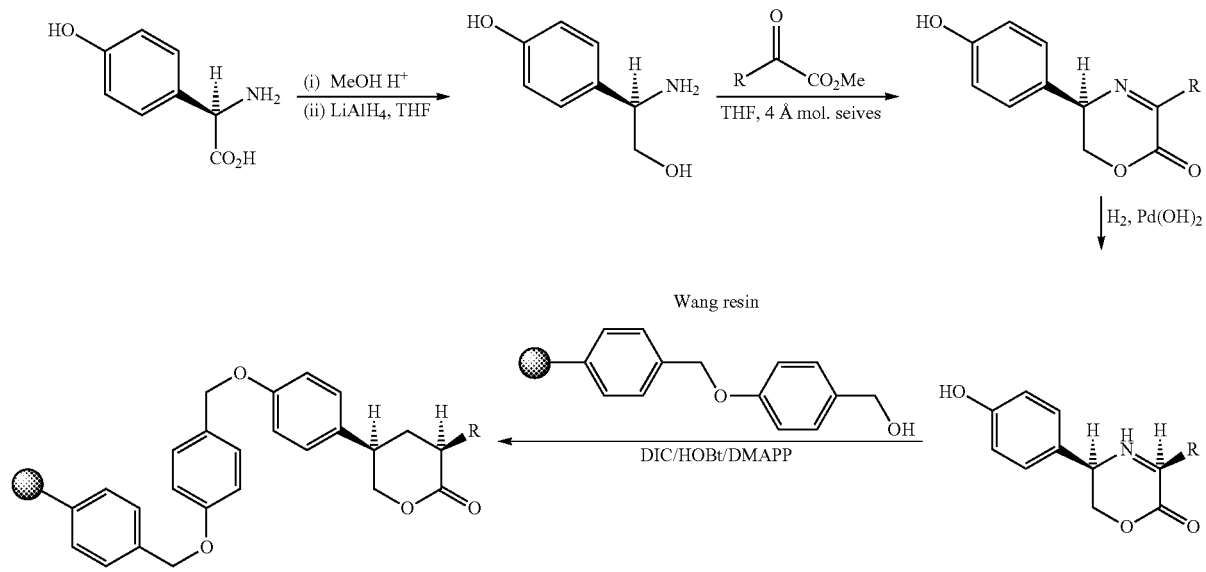

Example of a method to produce a thiomorpholinone template of formula (II)

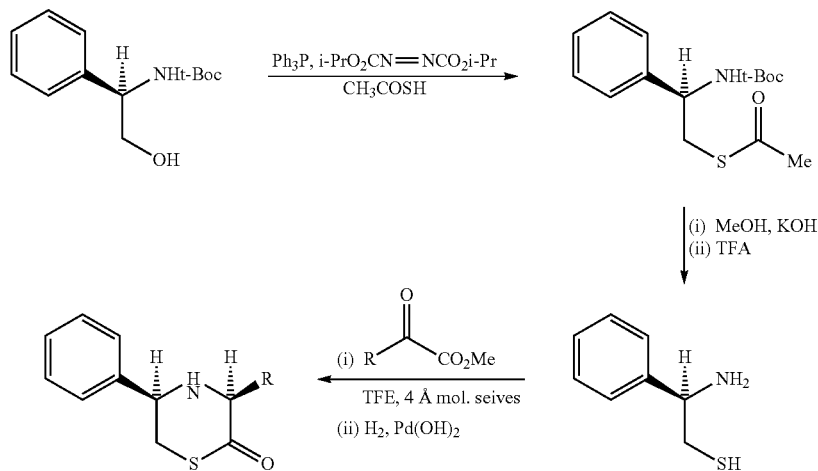

Examples of Peptide Synthesis (5R)-3-Methyl-5-phenyl-5,6-dihydro-2H-1,4-oxazin-2-one

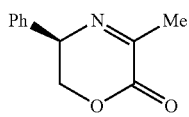

(R)-2-phenylglycinol (3.00 g, 21.9 mmol, 1.0 equiv.) and ethyl pyruvate (2.67 mL, 24.1 mmol, 1.1 equiv.) were refluxed in trifluoroethanol (50 mL) over activated 4 molecular sieves (8.00 g) for 24 hours. Filtration through a short pad of CELITE® diatomaceous earth and removal of solvent from the filtrate in vacuo generated the crude product which was purified by flash column chromatography on silica, eluting with petrol and diethyl ether (7:3) to furnish the title compound as a white solid (1.70 g, 41%); mp 71.0-72.0° C. (lit 71.0-72.0° C.); $v_{(max)}$(KBr) 3001 (C—H), 1734 (C=O), 1642 (C=N) cm$^{-1}$; $\delta_H$ (250 MHz, CDCl$_3$) 7.42-7.32 (5H, m, Ph), 4.89-4.80 (1H, m, PhCH), 4.56 (1H, dd, /4.49 Hz, T 11.55 Hz, 6β-H), 4.25 (1H, dd, J 10.97 Hz, T 11.51 Hz, 6α-H), 2.40 (3H, s, CH$_3$); $\delta_C$ (62.5 MHz, CDCl$_3$) 160.7, 155.9, 137.2, 129.4, 128.7, 127.5, 71.9, 60.1, 22.2; m/z (CL, NH$_3$), 189 (M$^+$, 25%), 159 (12%), 130 (24%), 104 (100%), 90 (21%), and 78 (6%); HRMS for C$_{11}$H$_{11}$NO$_2$ requires 189.0787 found 189.0782. $[\alpha]_D^{20}$ −2560.0 (c 1.11 CHCl$_3$) (lit $[\alpha]_D^{20}$ −237.1 (c 1.11 CHCl$_3$)).

(3S,5R)-3-Methyl-5-phenyl-3,4,5,6-tetrahydro-2H-1,4-oxazin-2-one

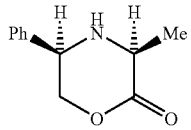

To a solution of (5R)-3-methyl-5-phenyl-5,6-dihydro-2H-1,4-oxazin-2-one (1.70 g, 9.0 mmol, 1.0 equiv.) in anhydrous dichloromethane (60 mL) under an atmosphere of nitrogen was added PtO$_2$ (170 mg, 0.1 equiv.). The mixture was consecutively degassed and purged three times with hydrogen and then stirred for 5 hours under an atmosphere of hydrogen. Filtration through a short pad of CELITE® diatomaceous earth and removal of solvent from the filtrate in vacuo yielded the crude product which was purified by recrystallisation in dichloromethane, diethyl ether and hexane to furnish the title compound as white needles (1.37 g, 80%); m.p. 82.0-83.0° C. (lit. m.p. 81.0-82.0° C.); $v_{(max)}$(KBr) 3314 (N—H), 2981 (C—H), 1739 (C=O), cm$^{-1}$, $\delta_H$ (250 MHz, CDCl$_3$) 7.44-7.33 (5H, m, Ph); 4.42-4.23 (3H, m, CHCH$_2$), 3.88 (1H, q, /6.76 Hz, CHCH$_3$), 1.86 (1H, br, NH), 1.50 (3H, d, J 6.16 Hz, CH$_3$); $\delta_c$ (62.5 MHz, CDCl$_3$) 170.7, 138.0, 129.3, 127.5, 127.2, 75.4, 58.2, 55.4, 19.0 m/z (CL, NH$_3$), 191 (M$^+$, 7%), 147 (20%), 131 (65%), 104 (100%), 91 (20%), and 77 (12%); HRMS for C$_{11}$H$_{13}$NO$_2$ requires 191.0943 found 191.0940. $[\alpha]_D^{20}$ –92.9 (c 1.02 CHCl$_3$) (lit. for the enantiomer $[\alpha]_D^{20}$ +92.3 (c 0.84 CHCl$_3$)).

(3S,5R)-4-N-Acetyl-3-methyl-5-phenyl-3,4,5,6,-tetrahydro-2H-1,4-oxazin-2-one

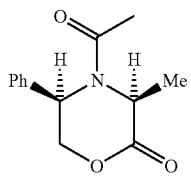

To a vigorously stirred mixture of (3S,5R)-3-methyl-5-phenyl-3,4,5,6-tetrahydro-2H-1,4-oxazin-2-one (300 mg, 1.56 mmol), Na$_2$CO$_3$ (500 mg, 4.68 mmol, 3.0 equiv.) in anhydrous dichloromethane (30 mL) was added acetyl chloride (0.17 mL, 2.34 mmol, 1.5 equiv.) dropwise over 1 min. The resulting solution was stirred for 15 minutes under an atmosphere of nitrogen. The reaction was quenched by the addition of saturated Na$_2$CO$_3$ (20 mL), the aqueous phase was extracted with diethyl diethyl ether (3×10 mL) and the combined extracts were dried over MgSO$_4$. The solvents were removed in vacuo and the crude material was purified by flash column chromatography on silica, eluting with diethyl ether and dichloromethane (9:1) to furnish the title compound as fine colourless needles (270 mg, 74%); m.p. 82-85° C.; $V_{(max)}$ (KBr) 2943 (C—H), 1733 (C=O, lactone), 1647 (C=O, amide) cm$^{-1}$; $\delta_H$ (250 Mhz, DMSO-d) 7.42-7.36 (5H, m, Ph), 5.49 (0.4H, PhCH×0.4) 5.33 (0.6H, PhCH×0.6), 5.08-5.05 (1H, m, CH$_3$CH), 4.65 (2H, d, J 6.10 Hz CH$_2$); 2.13 (1H, s, CH$_3$CON×1), 1.86 (2H, s, CH$_3$CON×2), 1.39 (3H, d, J 12.40 Hz CH$_3$CH): $\delta_c$ (62.5 MHz, DMSO—O 170.5, 169.8, 137.8, 129.4, 128.4, 127.1, 68.6, 55.5, 50.7, 49.7, 22.7, 19.0; $^m1_\tau$ (CL, NH$_3$), 234 (MH$^+$, 8%), 233 (M, 13%), 220 (4%), and 219 (100%); HRMS for C$_{13}$H$_{16}$NO$_3$ requires 234.1126. found 234.1130; $[\alpha]_D^{20}$ –29.8 (c 1.16 CHCl$_3$).

N-Fmoc-L-alanine acid chloride

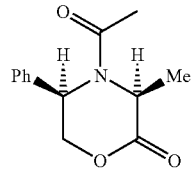

To a solution of N-Fmoc-L-alanine (2.00 g, 6.4 mmol, 1.0 equiv.) in anhydrous dichloromethane (40 mL) was added thionyl dichloride (4.70 ml, 64 mmol, 10 equiv.). The resulting mixture was refluxed for 2 hours under an atmosphere of nitrogen. The solvent and excess of thionyl chloride were removed in vacuo and the crude N-Fmoc-L-alanine acid chloride was partially purified by recrystallization from dichloromethane and hexane (1.74 g, 86%); m.p. 88-90° C. (lit. m.p. 112-114° C.); $v_{(max)}$ (KBr) 3328 (N—H), 3040 (C—H), 1778 (C=O, chloride), 1694 (C=O, carbamate), cm$^1$; $\delta_H$ (250 MHz, CDCl$_3$) 7.79-7.29 (8H, m, Fmoc), 5.22 (1H, d, J 8.0 Hz, NH), 4.67-4.38 (3H, m, CH$_3$CH×1, CHCH$_2$×2), 4.23 (1H, t, /6.52 Hz, CHCH$_2$); 1.55 (3H, d, J 7.28 Hz, CH$_3$CH); $\delta_c$ (62.5 MHz, CDCl$_3$) 176.8, 158.2, 143.9, 141.7, 128.2, 127.5, 125.3, 120.5, 67.7, 59.1, 47.5, 17.7; $^m1_z$ (CL, NH$_3$), 330 (MH$^+$, 48%), 258 (20%), 197 (65%), 154 (100%), 95 (20%), and 72 (12%); HRMS for C$_{18}$H$_{17}$ClNO$_3$ requires 330.1595 found 330.1592. $[\alpha]_D^{20}$ +8.50 (c 1.30 CHCl$_3$) (lit. $[\alpha]_D^{24}$ +4.03 (c 1.00 CH$_2$Cl$_2$)).

(3S,5R)—N—[N-Fmoc-(S)alanyl]-3-methyl-5-phenyl-3,4,5,6,-tetrahydro-2H-1,4-oxazin-2-one

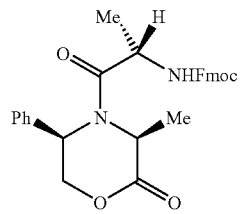

To a vigorously stirred mixture of (3S,5R)-3-methyl-5-phenyl-3,4,5,6-tetrahydro-2H-1,4-oxazin-2-one (600 mg, 3.14 mmol). Na$_2$CO$_3$ (1.70 g, 15.70 mmol, 5.0 equiv.) in 1:1 dichloromethane and water (40 mL) was added N-Fmoc-L-alanine acid chloride (1.26 g, 3.84 mmol, 1.2 equiv.) in dichloromethane (10 mL) dropwise over 5 min. The resulting solution was stirred for 2 hours. The aqueous phase was extracted with dichloromethane (3×15 mL). The combined extracts were washed with saturated Na$_2$CO$_3$ (50 mL), water (2×30 mL), brine (50 mL) and dried over MgSO$_4$. The solvents were removed in vacuo and the crude material was purified by flash column chromatography on silica, eluting with petrol and diethyl ether (1:4) to furnish the title compound as fine colorless needles (1.21 g, 80%); m.p. 89-90° C.; $V_{(max)}$ (KBr) 3321 (N—H)$_5$ 2983 (C—H), 1741 (C=O, lactone), 1718 (C=O, carbamate), 1654 (C=O, amide) cm$^{-1}$;

δ$_H$(250 MHz, DMSO-d) 7.91-7.27 (13H, m, Fmoc×8, Ph×5), 5.50 (1H, br, NH), 5.07 (1H, m, PhCH), 4.90 (1H, m, NCHCH$_3$); 4.77 (1H, d, 77.0 Hz, Cc-PhCHCH$_2$), 4.57 (2H, m, CHCH$_3$NH×1, β-PhCHCH$_2$×1), 4.26 (1H, m, OCH$_2$CH), 4.19 (2H, m, OCH$_2$CH), 1.28 (3H, d, /4.O Hz$_5$ NCHCH$_3$), 1.10 (3H, d, /4.0 Hz, CHCH$_3$NH); δ$_c$ (62.5 MHz, OMSO-d) 172.0, 170.0, 156.1, 144.2, 141.1, 136.2, 128.9, 128.3, 127.9, 127.4, 126.7, 125.7, 120.4, 66.0, 65.3, 53.0, 50.7, 47.8, 46.9, 18.6, 17.8; $^m1_z$ (Cl, NH$_3$), 508 (MNa$^+$, 6%), 502 (MNH$_4^+$, 45%), 487 (4%), and 485 (MH$^+$, 100%); HRMS for C$_{29}$H$_{29}$N$_2$O$_5$ requires 485.2069. found 485.2060; [α]$_D^{20}$ −13.1 (c1.06 CHCl$_3$).

(5S)-3-Methyl-5-phenyl-5,6-dihydro-2H-1,4-oxazin-2-one

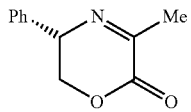

(S)-2-phenylglycinol (3.00 g, 21.9 mmol, 1.0 equiv.) and ethyl pyruvate (2.67 mL, 24.1 mmol, 1.1 equiv.) were refluxed in trifluoroethanol (50 mL) over activated 4 molecular sieves (8.00 g) for 24 hours. Filtration through a short pad of CELITE® diatomaceous earth and removal of solvent from the filtrate in vacuo generated the crude product which was purified by flash column chromatography on silica, eluting with petrol and diethyl ether (7:3) to furnish the title compound as a white solid (1.83 g, 44%); m.p. 70.0-71.0° C. (lit 71.0-72.0° C.); ν$_{(max)}$(KBr) 3007 (C—H), 1735 (C=O), 1640 (C=N) cm$^{-1}$; δ$_H$ (250 MHz, CDCl$_3$) 7.45-7.32 (5H, m, Ph), 4.88-4.81 (1H, m, PhCH), 4.56 (1H, dd, J 4.49 Hz, T 9.48 Hz, 6β-H), 4.25 (1H, dd/13.01 Hz, JT 14.99 Hz, 6α-H), 2.41 (3H, s, CH$_3$); δ$_c$ (62.5 MHz CDCl$_3$) 160.7, 155.9, 137.2, 129.4, 128.7, 127.5, 71.9, 60.1, 22.2; m/z (CL, NH$_3$), 189 (M$^+$, 25%), 159 (12%), 130 (24%), 104 (100%), 90 (21%), and 78 (6%); HRMS for C$_{11}$H$_n$NO$_2$ requires 189.0787 found 189.0782. [α]$_D^{20}$ +253.0 (c 0.98 CHCl$_3$) (the enantiomer lit. [α]$_D^{20}$ −237.1 (c 1.11 CHCl$_3$)).

(3S)-3-Methyl-5-phenyl-3,4,5,6-tetrahydro-2H-1,4-oxazin-2-one

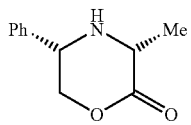

To a solution of (5S)-3-methyl-5-phenyl-5,6-dihydro-2H-1,4-oxazin-2-one (1.70 g, 9.0 mmol, 1.0 equiv.) in anhydrous dichloromethane (60 mL) under an atmosphere of nitrogen was added PtO$_2$ (170 mg, 0.1 equiv.). The mixture was consecutively degassed and purged three times with hydrogen and then stirred for 5 hours under an atmosphere of hydrogen. Filtration through a short pad of CELITE® diatomaceous earth and removal of solvent from the filtrate in vacuo yielded the crude product which was purified by recrystallisation in dichloromethane, diethyl ether and hexane to furnish the title compound as white needles (1.26 g, 74%); m.p. 81.0-82.0° C. (lit. m.p. 81.0-82.0° C.); ν$_{(max)}$(KBr) 3314 (N—H), 2981 (C—H), 1736 (C=O), cm$^{-1}$; δ$_H$ (250 MHz, CDCl$_3$) 7.43-7.26 (5H, m, Ph); 4.42-4.23 (3H, m, CHCl$_2$), 3.88 (1H, q, /6.76 Hz, CHCH$_3$), 1.80 (1H, br, NH), 1.50 (3H, d, J 6.76 Hz, CH$_3$); δ$_c$ (62.5 MHz, CDCl$_3$) 170.7, 138.1, 129.3, 129.1, 127.5, 75.4, 58.2, 55.4, 19.0; m/z (CL, NH$_3$), 192 (MH$^+$, 30%), 147 (68%), 132 (64%), 104 (100%), and 91 (10%); HRMS for C$_{11}$H$_{13}$NO$_2$ requires 192.1025 found 192.1019. [α]$_D^{20}$ +88.8 (c 0.96 CHCl$_3$) (lit. [α]$_D^{20}$ +92.3 (c 0.84 CHCl$_3$)).

(3R,5S)—N—[N-Fmoc(S)alanyl]-3-methyl-5-phenyl-3,4,5,6-tetrahydro-2H-1,4-oxazin-2-one

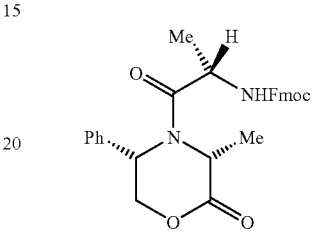

To a vigorously stirred mixture of (3R,5S)-3-methyl-5-phenyl-3,4,5,6-tetrahydro-2H-1,4-oxazin-2-one (500 mg, 2.62 mmol), Na$_2$CO$_3$ (1.40 g, 13.3 mmol, 5.0 equiv.) in 1:1 dichloromethane and water (40 mL) was added N-Fmoc-L-alanine acid chloride (1.04 g, 3.14 mmol, 1.2 equiv.) in dichloromethane (10 mL) dropwise over 5 min. The resulting solution was stirred for 2 hours. The aqueous phase was extracted with dichloromethane (3×15 mL). The combined extracts were washed with saturated Na$_2$CO$_3$ (50 mL), water (2×30 mL), brine (50 mL) and dried over MgSO$_4$. The solvents were removed in vacuo and the crude material was purified by flash column chromatography on silica, eluting with petrol and diethyl ether (1:4) to furnish the title compound as fine colourless needles (1.02 g, 80%); m.p. 87-88° C.; ν$_{(max)}$(KBr) 3323 (N—H), 2982 (C—H), 1761 (C=O, lactone), 1717 (C=O, carbamate), 1656 (C=O, amide) cm$^{-1}$; δ$_H$ (400 MHz. DMSO-d, 110° C.) 7.84-7.29 (13H, m, Fmoc×8, Ph×5), 7.08 (1H, br, NH), 5.54 (1H, t, /5.88 Hz, PhCH), 4.96 (1H, q, /7.11 Hz NCHCH$_3$); 4.68-4.60 (2H, m, PhCHCH$_2$), 4.41-4.32 (3H, m, CHCH$_3$NH×1, OCH$_2$CH×2), 4.22 (1H, t, /6.72 Hz OCH$_2$CH), 1.45 (3H, d, /7.15 Hz, NCHCH$_3$), 1.08 (3H, d, /6.71 Hz, CHCH$_3$NH); δ$_c$(62.5 MHz, OMSO-d) 174.0, 172.8, 170.4, 169.6, 156.3, 144.1, 141.1, 137.7, 129.4, 128.7, 128.0, 127.4, 127.3, 127.1, 125.6, 120.5, 68.8, 66.0, 55.5, 55.3, 52.2, 51.4, 50.0, 47.2, 20.5, 18.6, 17.7, 17.1; $^m1_z$ (C.I. NH$_3$), 485 (MH$^+$, 12%), 431 (8%), 381 (7%), 281 (15%) and 149 (100%); HRMS for C$_{29}$H$_{29}$N$_2$O$_5$ requires 485.2069. found 485.2076; [α]$_D^{20}$ +22.2 (c 0.94 CHCl$_3$).

(5R)-3-Isopropyl-5-phenyl-5,6-dihydro-2H-1,4-oxazin-2-one

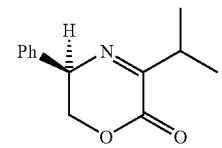

(R)-2-phenylglycinol (4) (2.00 g, 14.6 mmol, 1.0 equiv.) and ethyl 3-methyl-2-oxobutyrate (2.20 mL, 14.6 mmol. 1.0 equiv.) were refluxed in trifluoroethanol (30 mL) over activated 4 molecular sieves (7.0 g) for 24 hours. Filtration through a short pad of CELITE® diatomaceous earth and removal of solvent from the filtrate in vacuo generated the crude product which was purified by flash column chromatography on silica, eluting with petrol and diethyl ether (4:1) to furnish the title compound as a colourless oil (1.13 g, 36%); $v_{(max)}$(film) 2965 (C—H), 1740 (C=O), 1638 (C=N) cm$^{-1}$; $\delta_H$ (250 MHz, CDCl$_3$) 7.45-7.32 (5H, m, Ph), 4.90-4.83 (1H, m, PhCH), 4.55 (1H, dd, J 4.4 Hz, T 11.5 Hz, 6β-H), 4.13 (1H, dd/10.9 Hz, T 11.4 Hz, 6α-H), 3.32 (1H, m, CH(CH$_3$)$_2$), 1.25 (3H, d, J 5.0 Hz, CH(CH$_3$)$_2$×3), 1.22 (3H, d, /5.0 Hz, CH(CH$_3$)$_2$×3); $\delta_c$ (62.5 MHz, CDCl$_3$) 167.7, 155.7, 137.5, 129.3, 128.6, 127.4, 71.7, 59.7, 32.7, 20.7, 19.9: m/z (CL, NH$_3$), 220 (100%), 218 (MH$^+$, 17%), 217 (27%), and 216 (25%); HRMS for C$_{13}$H$_{16}$NO$_2$ requires 218.1177 found 218.1181. $[\alpha]_D^{20}$ −207.5 (c 1.17 CHCl$_3$).

(3S,5R)-3-Isopropyl-5-phenyl-3,4,5,6-tetrahydro-2H-1,4-oxazin-2-one (39)

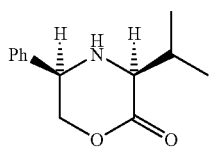

To a solution of (5R)-3-isopropyl-5-phenyl-5,6-dihydro-2H-1,4-oxazin-2-one (38) (1.03 g, 4.74 mmol, 1.0 equiv.) in anhydrous dichloromethane (50 mL) under an atmosphere of nitrogen was added PtO$_2$ (103 mg, 0.1 equiv.). The mixture was consecutively degassed and purged three times with hydrogen and then stirred for 5 hours under an atmosphere of hydrogen. Filtration through a short pad of CELITE® diatomaceous earth and removal of solvent from the filtrate in vacuo yielded the crude product which was purified by flash column chromatography on silica eluting with petrol and diethyl ether (4:1) to furnish the title product as a waxy solid (662 mg, 64%); m.p. 61.5-62.5° C.; $v_{(max)}$(KBr) 3326 (N—H—), 2960 (C—H), 1733 (C=O), cm$^{-1}$; $\delta_H$ (250 MHz, CDCl$_3$) 7.47-7.35 (5H, m, Ph); 4.33-4.18 (3H, m, PhCHCH$_2$), 3.81 (1H, m, NHCH), 2.49, (1H, m, CH(CH$_3$)$_2$), 1.68 (1H, br, NH), 1.09 (3H, dd, J 6.75 Hz, CH(CH$_3$)$_2$×3), 1.05 (3H, dd, J 6.75 Hz, CH(CH$_3$)$_2$×3); $\delta_C$, (62.5 MHz, CDCl$_3$) 170.3, 138.5, 129.3, 129.1, 127.6, 74.9, 64.2, 57.3, 32.0, 19.4, 17.4; m/z (Cl, NH$_3$), 237 (MNH$_4^+$, 5%), 220 (100%, MH$^+$), 219 (22%), and 216 (6%); HRMS for C$_{13}$H$_{18}$NO$_2$ requires 220.1333 found 220.1338. $[\alpha]_D^{20}$ −92.1 (c 1.45 CHCl$_3$).

(3S,5R)—N—[N-Fmoc-(S)alanyl]-3-isopropyl-5-phenyl-3,4,5,6,-tetrahydro-2H-1,4-oxazin-2-one

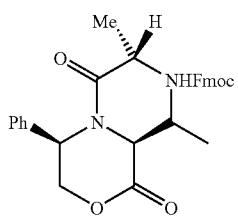

Method 1:

To a solution of (3S,5R)-3-isopropyl-5-phenyl-3,4,5,6-tetrahydro-2H-1,4-oxazin-2-one (150 mg, 0.68 mmol) in anhydrous dichloromethane (10 mL) was added N-Fmoc-L-alanine acid chloride (276 mg, 0.82 mmol, 1.2 equiv.) in anhydrous dichloromethane (5 mL). The resulting solution was stirred for 24 hours. The solvent was removed in vacuo and the crude material was purified by flash column chromatography on silica, eluting with petrol and diethyl ether (2:3) to furnish the title product as colourless fine needles (95 mg, 27%).

Method 2:

To a vigorously stirred solution of (3S,5R)-3-isopropyl-5-phenyl-3,4,5,6-tetrahydro-2H-1,4-oxazin-2-one (200 mg, 0.91 mmol) and Na$_2$CO$_3$ (415 mg, 2.73 mmol, 3.0 equiv.) in anhydrous dichloromethane (15 mL) was added N-Fmoc-L-alanine acid chloride (428 mg, 1.36 mmol, 1.5 equiv.) in anhydrous dichloromethane (10 mL). The resulting mixture was stirred under nitrogen for 1 hour. Filtration through a short pad of CELITE® diatomaceous earth and removal of solvent from the filtrate in vacuo furnished the crude material which was purified by flash column chromatography on silica, eluting with petrol and diethyl ether (3:7) to furnish the title product as colourless fine needles (380 mg, 82%); m.p. 72-75° C.; $v_{(max)}$(KBr) 3402 (N—H), 2969 (C—H), 1760 (C=O, lactone), 1718 (C=O, carbamate), 1654 (C=O, amide) cm$^{-1}$; $\delta_H$ (250 MHz, CDCl$_3$) 7.65-7.15 (13H, m, Fmoc×8, Ph×5), 5.46 (1H, br, NH), 5.03-4.98 (1H, m, PhCH), 4.75 (1H, d, /10.0 Hz CHCH(CH$_3$)$_2$), 4.32-4.13 (3H, m, PhCHCH$_2$ and OCH$_2$CH), 4.07-4.02 (1H, m, CHCH$_3$), 3.89-3.79 (2H, m, OCH$_2$CH), 2.18-2.00 (1H, m, CH(CH$_3$)$_2$), 1.21 (3H, d, J 5.5 Hz, CH(CH$_3$)$_2$×3), 1.19 (3-H, d, /5.0 Hz, CHCH$_3$), 1.02 (3H, d, J 6.5 Hz, CH(CH$_3$)$_2$×3); $\delta_c$ (62.5 MHz, CDCl$_3$) 174.1, 167.1, 153.7, 142.8, 140.2, 134.9, 128.8, 128.2, 127.2, 124.9, 124.1, 118.9, 66.3, 65.7, 55.2, 52.5, 47.5, 45.0, 31.6, 20.1, 18.2, 17.8; m/z (Cl, NH$_3$), 535 (MNa$^+$, 73%), 513 (MH$^+$, 100%), 334 (11%), 333 (53%), 328 (23%), and 311 (19%); (Cl.) HRMS for C$_{31}$H$_{33}$N$_2$O$_5$ requires 513.2381. found 513.2378. $[\alpha]_D^{20}$ −22.1 (c 1.05 CHCl$_3$).

N-Fmoc-L-valine acid chloride

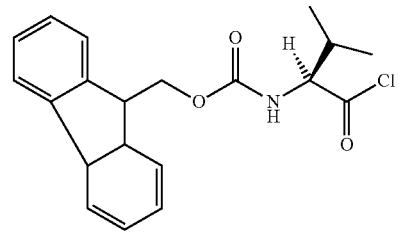

To a solution of N-Fmoc-L-alanine (3.00 g, 8.7 mmol, 1.0 equiv.) in anhydrous dichloromethane (40 mL) was added thionyl chloride (6.5 mL, 87 mmol, 10.0 equiv.). The resulting mixture was refluxed for 2 hours under an atmosphere of nitrogen. The solvent and excess of thionyl dichloride were removed in vacuo and the crude N-Fmoc-L-alanine acid chloride was partially purified by recrystallization from dichloromethane and hexane (2.50 g, 80%); m.p. 75-79° C. (lit. m.p. 111-112° C.); $v_{(max)}$(KBr) 3317 (N—H), 2969 (C—H), 1788 (C=O, acid chloride), 1696 (C=O, carbamate), cm$^{-1}$; $\delta_H$ (250 MHz, CDCl$_3$) 7.78-7.29 (8H, m, Fmoc), 5.20 (1H, d, J 9.5 Hz, NH), 4.55-4.33 (3H, m, CH$_3$CH×1, CHCH$_2$×2), 4.23 (1H, t, J 6.5 Hz, CHCH$_2$); 2.40 (1H, m, CH(CH$_3$)$_2$), 1.05 (3H, d, J 7.0 Hz, CH(CHg)$_2$×3), 0.95 (3H, d, /7.0 Hz, CH(CHb)$_2$× 3); δ$_c$ (62.5 MHz, CDCl$_3$) 175.4, 157.1, 143.9, 141.8, 128.2, 127.5, 125.3, 120.5, 68.2, 67.7, 47.5, 30.3 19.7, 17.4; [α]$_D^{20}$ +13.2 (c 1.05 CHCl$_3$) (lit. [α]$_D^{24}$ +5.5 (c 1.00 CH$_2$Cl$_2$)).

(3S,5R)—N—[N-Fmoc-(S)valinyl]-3-isopropyl-5-phenyl-3,4,5,6,-tetrahydro-2H-1,4-oxazin-2-one

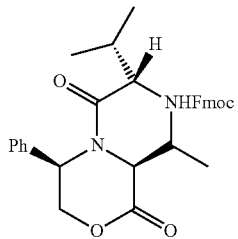

Method 1:

To a solution of (3S,5R)-3-wøpropyl-5-phenyl-3,4,5,6-tetrahydro-2H-1,4-oxazin-2-one (200 mg, 0.91 mmol) in anhydrous dichloromethane (20 mL) was added N-Fmoc-L-valine acid chloride (391 mg, 1.10 mmol, 1.2 equiv.) in anhydrous dichloromethane (5 mL). The resulting solution was stirred for 24 hours. The solvent was removed in vacuo and the crude material was purified by flash column chromatography on silica, eluting with petrol and diethyl ether (2:3) to furnish the title product as colourless fine needles (80 mg, 16%).

Method 2:

To a vigorously stirred solution of (3S,5R)-3-isopropyl-5-phenyl-3,4,5,6-tetrahydro-2H-1,4-oxazin-2-one (200 mg, 0.91 mmol) and Na$_2$CO$_3$ (415 mg, 2.73 mmol, 3.0 equiv.) in anhydrous dichloromethane (15 mL) was added N-Fmoc-L-valine acid chloride (533 mg, 1.36 mmol, 1.5 equiv.) in anhydrous dichloromethane (10 mL). The resulting mixture was stirred under nitrogen for 6 hours. Filtration through a short pad of CELITE® diatomaceous earth and removal of solvent from the filtrate in vacuo furnished the crude material which was purified by flash column chromatography on silica, eluting with petrol and diethyl ether (1:1) to furnish the title product as colourless fine needles (260 mg, 52%); m.p. 75-78° C.; ν$_{(max)}$(KBr) 3421 (N—H), 2966 (C—H), 1763 (C=O, lactone), 1718 (C=O, carbamate), 1654 (C=O, amide) cm$^{-1}$; δ$_H$ (400 MHz, DMSO-d$_6$, 120° C.) 7.83-7.25 (13H, m, Fmoc×8, Ph×5), 6.81 (1H, br, NH), 5.34 (1H, dd, /6.2 Hz, /10.8 Hz, PhCH), 4.77 (1H, d, /9.5 Hz, NCH), 4.58 (1H, dd, J 6.2 Hz, /12.5 Hz, PhCHCH$_2$×1), 4.47 (1H, dd, J 10.8 Hz, J 12.4 Hz, PhCHCH$_2$×1), 4.32-4.28 (1H, m, CH$_3$CH), 4.24-4.15 (3H, m, OCH$_2$Cl), 2.22-2.05 (2H, m, CH—(CH$_3$)$_2$×2), 1.18 (3H, d, J 6.5 Hz, CH(CH$_3$)$_2$×3), 0.96 (3H, d, J 6.5 Hz, CHCH$_3$), 0.84 (6H, t, J 7.0 Hz, CH(CH$_3$)$_2$× 6); δ$_c$ (62.5 MHz, CDCl$_3$) 174.5, 168.5, 155.5, 144.2, 141.7, 130.2, 129.6, 128.1, 127.4, 126.7, 126.4, 125.5, 120.4, 68.0, 67.1, 61.3, 57.7, 57.0, 47.4, 33.2, 32.6, 21.8, 20.1, 19.7, 18.4, 17.5; m/z (CL), 614 (100%), 576 (50%), 564 (9%), 541 (MH$^+$), 519 (22%), and 503 (16%); HRMS for C$_{33}$H$_{37}$N$_2$O$_5$ requires 541.2692 found 541.2709. [α]$_D^{20}$ −28.5 (c 0.56 CHCl$_3$).

Phenacyl N-tert-butoxycarboxyl-(S)-phenylalanate

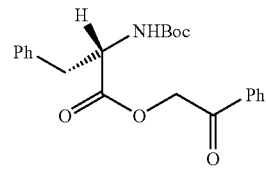

To a solution of potassium hydroxide (0.64 g, 11.31 mmol) in methanol (15 mL) was added Boc-L-phenylalanine (3.00 g, 11.31 mmol). The resulting solution was stirred at room temperature for 3 hours. The solvent was removed and the crude material was dried in vacuo to yield white powder which was subsequently added in anhydrous N,N-dimethylformamide (15 mL) and treated with 2-bromoacetophenone (2.07 g, 13.57 mmol, 1.2 equiv.). The resulting solution was stirred at room temperature under nitrogen for 24 hours and was quenched by addition of water (20 mL). The precipitate can be either used as crude in next step or purified by recrystallization from diethyl ether yield the title compound as white fine needles (3.55 g, 82%); mp 140.0-141.0° C.; ν$_{(max)}$ (KBr) 3395 (N—H), 2973 (C—H), 1757 (C=O, ester), 1715 (C=O, ketone), 1692 (C=O, carbamate) cm$^{-1}$: δ$_H$(250 MHz CDCl$_3$) 7.93-7.24 (10H, m, Ph), 5.50 (1H, d, /16.4 Hz, OCH$_2$×1), 5.31 (1H, d, /16.4 Hz, OCH$_2$×1), 4.97 (1H, d, J 18.1 Hz, NH), 4.75 (1H, dd, /7.2 Hz, r 6.1 Hz, CH), 3.36 (1H, dd, /5.4 Hz, r 14.1 Hz, PhCH$_2$×1), 3.14 (1H, dd, /7.1 Hz, /" 14.0 Hz, PhCH$_2$×1), 1.40 (9H, s, f-butyl); δ$_c$ (62.5 MHz, CDCl$_3$) 191.9 172.0, 155.6, 136.5, 134.4, 129.9, 129.3, 129.0, 128.2, 127.4, 80.4, 66.8, 54.7, 38.6, 28.7. [α]$_D^{20}$ −7.9 (c 1.01 CHCl$_3$).

(3S)-3-Benzyl-5-phenyl-3,6-dihydro-2H-1,4-oxazin-2-one

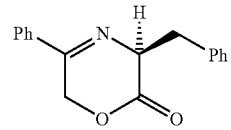

To a suspension of phenacyl N-tert-butoxycarboxyl-(S)-phenylalanate (3.51 g, 9.16 mmol) in diethyl ether (150 mL) was added hydrogen bromide in acetic acid (33% w/w, 4.8 mL, 27.5 mmol, 3.0 equiv.). The resulting mixture was stirred under nitrogen for 3 hours during which time another portion of diethyl ether (100 mL) was added. The solid was separated by filtration through a sinter, washed with diethyl ether (2×30 ml) and dried in vacuo to furnish the amino ester hydrobromide which was subsequently dissolved in pH 5 acetate buffer (100 mL, 0.2 M, prepared from 70 parts 0.2 M aqueous sodium acetate and 30 parts 0.2 M aqueous acetic acid). The resulting mixture was stirred under nitrogen for 12 hours during which time yellow oil was formed. The precipitate can be either used as crude in next step or purified by flash column chromatography on silica, eluting with petrol and diethyl ether (3:2) to furnish the title compound as white solid (1.56 g, 65%); ν$_{(max)}$ (KBr) 2932 (C—H), 1751 (C=O), cm$^{-1}$; m.p. 57.0-59.0° C. (lit. 58.0-60.0° C.)[63]; δ$_H$ (250 MHz, CDCl$_3$) 7.90-7.18 (1OH, m, Ph), 5.01 (1H, d, /14.2 Hz, CHCH$_2$O×1), 4.83 (H, m, CHCH$_2$Ph), 4.06 (1H, m, CHCH$_2$), 4.11 (1H, d, J 14.2 Hz, CHCH₂O×1), 3.46 (1H, dd, /5.45 Hz, /13.5 Hz, CHCH₂Ph×1), 3.32 (1H, dd, /5.45 Hz, /13.5 Hz, CHCH₂Ph×1); $\delta_c$ (62.5 MHz, CDCl₃) 169.0, 162.8, 136.6, 134.7, 131.7, 130.6, 129.2, 128.8, 127.6, 126.3, 67.8, 61.0, 39.4; % (CL, NH₃), 266 (32%), 265 (M⁺, 100%), 264 (42%), 263 (5%) and 262 (3%); HRMS for C₁₇H₁₅NO₂ requires 265.1103. found 265.1108. $[\alpha]_D^{20}$ +85.1 (c 1.04 CHCl₃) (lit. $[\alpha]_D^{20}$ +85.7 (c 2.00 CHCl₃)).

(3S,5R)-3-benzyl-5-phenyl-3,4,5,6-tetrahydro-2H-1,4-oxazin-2-one

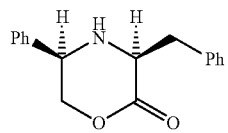

To a solution of (3S)-3-Benzyl-5-phenyl-3,6-dihydro-2H-1,4-oxazin-2-one (1.56 g, 5.88 mmol, 1.0 equiv.) in anhydrous methanol (40 mL) under an atmosphere of nitrogen was added palladium on activated carbon (156 mg, 0.1 equiv. by mass). The mixture was consecutively degassed and purged three times with hydrogen and then stirred for 5 hours under an atmosphere of hydrogen. Filtration through a short pad of CELITE® diatomaceous earth and removal of solvent from the filtrate in vacuo yielded the crude product which was purified by flash column chromatography on silica eluting with petrol and diethyl ether (4:1) to furnish the title product as a white solid (514 mg, 33%); m.p. 75.0-76.0° C. (lit. 76.0-78.0° C.); $v_{(max)}$(KBr) 3321 (N—H), 2949 (C—H), 1731 (C=O), cm⁻¹; $\delta_H$ (250 MHz, CDCl₃) 7.36-7.21 (10H, m, Ph), 4.34-4.15 (3H, m, PhCHCH₂), 3.97 (1H, dd, J 3.2, T 10.0 Hz, NHCH), 3.56, (1H, dd, J 3.2, J 13.6 Hz, CHPh×1), 3.00, (1H, dd, /10.0, T 13.6 Hz, CH₂Ph×1), 1.84 (1H, br, NH); $\delta_H$, (62.5 MHz, CDCl₃) 169.6, 138.0, 137.8, 129.8, 129.3, 129.2, 129.1, 127.5, 127.4, 75.3, 60.6, 57.9, 39.4; m/z (CL, NH₃), 268 (MH⁺, 40%), 267 (80%, M⁺), 223 (100%), and 209 (57%); HRMS for C₁₇H₁₇NO₂ requires 267.1259 found 267.1263. $[\alpha]_D^{20}$ −156.4 (c 1.02 CHCl₃) (lit. $[\alpha]_D^{20}$ −157.9 (c 2.00 CHCl₃)).

(3S,5R)—N—[N-Fmoc-(S)-alanyl]-3-benzyl-5-phenyl-3,4,5,6,-tetrahydro-2H-1,4-oxazin-2-one

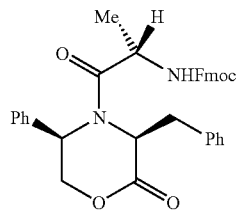

To a vigorously stirred solution of (3S,5R)-3-benzyl-5-phenyl-3,4,5,6-tetrahydro-2H-1,4-oxazin-2-one (200 mg, 0.75 mmol) and Na₂CO₃ (239 mg, 2.25 mmol, 3.0 equiv.) in anhydrous dichloromethane (20 mL) was added N-Fmoc-L-alanine acid chloride (354 mg, 1.12 mmol, 1.5 equiv.) in anhydrous dichloromethane (6 mL). The resulting mixture was stirred under nitrogen for 4 hours. Filtration through a short pad of CELITE® diatomaceous earth and removal of solvent from the filtrate in vacuo furnished the crude product which was purified by flash column chromatography on silica, eluting with petrol and diethyl ether (2:3) to furnish the title product as colourless fine needles (150 mg, 36%); m.p. 87-89° C.; $v_{(max)}$(KBr) 3413 (N—H), 2981 (C—H), 1760 (C=O, lactone), 1718 (C=O, carbamate), 1656 (C=O, amide) cm⁻¹; $\delta_H$ (400 MHz, DMSO-d, 100° C.) 7.90-7.27 (18H, m, Fmoc×8, Ph×10), 7.07 (1H, br, NH), 5.47 (1H, dd, /4.8 Hz, /7.6 Hz, PhCH), 5.32 (1H, t, J 7.2 Hz, NCH), 4.82 (1H, dd, /7.6 Hz, J 12.4 Hz, PhCHCH₂×1), 4.71 (1H, dd, J 12 Hz, J' 12.4 Hz, PhCHCH₂×1), 4.41 (1H, q, J 6.4 Hz, CH₃CH), 4.37-4.21 (3H, m, OCH₂CH), 3.15 (2H, d, /6.8 Hz, CH₂Ph), 1.21 (3H, d, /6.8 Hz, CH₃); $\delta_c$ (62.5 MHz, CDCl₃) 174.8, 170.8, 168.8, 159.6, 155.0, 142.7, 140.2, 128.9, 128.5, 127.9, 127.6, 127.4, 126.9, 126.6, 126.1, 124.2, 119.0, 66.2, 62.1, 61.0, 52.5, 47.8, 45.9, 33.8, 15.6; m/z (CL), 560 (M⁺), 502 (100%), 464 (43%), 426 (19%), and 414 (83%); HRMS for C₃₅H₃₂N₂O₅ requires 560.2303 found 560.2293. $[\alpha]_D^{20}$ −56.2 (c 1.01 CHCl₃).

(3S,5R)—N—[N-Fmoc-(S)-alanyl]-3-tert-butyl-5-phenyl-3,4,5,6,-tetrahydro-2H-1,4-oxazin-2-one

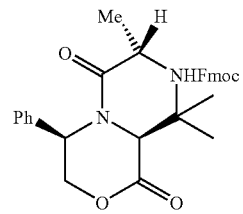

To a vigorously stirred solution of (3S,5R)-3-tert-butyl-5-phenyl-3,4,5,6-tetrahydro-2H-1,4-oxazin-2-one (150 mg, 0.63 mmol) in anhydrous dichloromethane (15 mL) and Na₂CO₃ (341 mg, 3.22 mmol, 5.0 equiv.) was added N-Fmoc-L-alanine acid chloride (298 mg, 0.95 mmol, 1.5 equiv.). The resulting mixture was stirred under an atmosphere of nitrogen for 18 hours. Filtration through a short pad of CELITE® diatomaceous earth and removal of solvent from the filtrate in vacuo gave the crude material which was purified by flash column chromatography on silica, eluting with petrol and diethyl ether (1:1) to furnish the title product as colourless fine needles (170 mg, 51%); m.p. 74-75° C.; $v_{(max)}$(KBr) 2976 (C—H), 1752 (C=O, lactone), 1724 (C=O, carbamate), 1662 (C=O, amide) cm⁻¹; $\delta_H$ (250 MHz, DMSO-d₆) 7.90-7.29 (13H, m, Fmoc×8, Ph×5), 5.39 (1H, br, PhCH), 4.62 (2H, br, CH₂O), 4.33 (1H, br, CH₃CH), 4.18 (3H, br, OCH₂CH), 1.23 (3H, d, /6.70 Hz, CHCH₃), 0.88 (9H, s, OCH); $\delta_c$, (62.5 MHz, DMSO-d₆) 175.9, 168.1, 155.8, 144.2, 144.1, 141.0, 137.1, 129.0, 128.0, 127.4, 125.8, 125.7, 120.4, 66.0, 62.2, 55.3, 53.0, 48.7, 46.9, 37.0, 28.6, 17.4; m/z (CL): 528 (15%), 527 (MB⁺, 34%), 526 (M, 100%), 470 (62%), and 414 (74%); HRMS for C₃₂H₃₄N₂O₅ requires 526.459 found 526.2457. $[\alpha]_D^{20}$ −10.9 (c 1.20 CHCl₃).

(3S,5R)—N—[N-Fmoc-(S)valinyl]-3-tert-butyl-5-phenyl-3,4,5,6,-tetrahydro-2H-1,4-oxazin-2-one

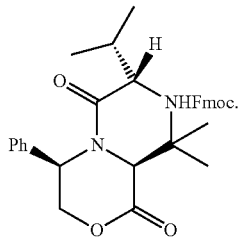

To a vigorously stirred solution of (3S,5R)-3-tert-butyl-5-phenyl-3,4,5,6-tetrahydro-2H-1,4-oxazin-2-one (75 mg, 0.32 mmol) in anhydrous dichloromethane (7 mL) and $Na_2CO_3$ (170 mg, 1.61 mmol, 5.0 equiv.) was added N-Fmoc-L-valine acid chloride (170 mg, 0.48 mmol, 1.5 equiv.). The resulting mixture was stirred under an atmosphere of nitrogen for 48 hours. Filtration through a short pad of CELITE® diatomaceous earth and removal of solvent from the filtrate in vacuo gave the crude material which was purified by flash column chromatography on silica, eluting with petrol and diethyl ether (1:1) to furnish the title product as colourless fine needles (32 mg, 18%); m.p. 71-73° C.; $v_{(max)}$(KBr) 2964 (C—H), 1752 (C=O, lactone), 1734 (C=O, carbamate), 1655 (C=O, amide) cm$^{-1}$; $\delta_H$ (250 MHz, CDCl$_3$) 7.77-7.25 (13H, m, Fmoc×8, Ph×5), 5.30 (1H, br, $(CH_3)_2$CHCH), 5.13 (1H, t, J 10.0 Hz, PhCH), 4.52-4.38 (2H, m, PhCHCH$_2$O), 4.29-4.21 (1H, n, OCH$_2$CH), 4.15 (3H, br, OCH$_2$CH×2 and CHC(CH$_3$)$_3$), 1.99-1.96 (1H, m, $(CH_3)_2$CH), 1.22 (9H, s, C(CH$_3$)$_3$); 0.97-0.84 (6H, m, $(CH_3)_2$CH); $\delta_c$ (62.5 MHz, CDCl$_3$) 175.9, 168.4, 155.4, 144.2, 141.7, 136.5, 130.2, 129.2, 128.1, 127.6, 126.4, 125.5, 120.4, 68.3, 67.1, 64.3, 57.6, 56.5, 47.5, 38.0, 32.7, 30.7, 20.2, 17.4; m/z (CL), 554 (MH$^+$, 14%), 502 (100%), 464 (40%), 426 (20%), and 414 (74%); HRMS for $C_{34}H_{38}N_2O_5$ requires 554.2781 found 554.2790. $[\alpha]_D^{20}$ −17.5 (c 1.48 CHCl$_3$).

N-t-Boc-(S)-alanyl-N-(1-phenyl-2-hydroxylethyl)glycyl-(S)-alanine tert-butyl ester

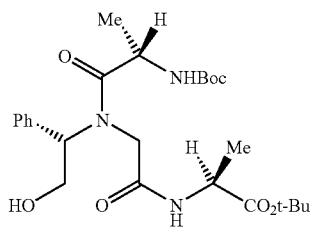

To a suspension of L-alanine t-butyl ester hydrochloride (408 mg, 2.3 mmol) and (5S)-4-[N-?-Boc-(S)-alanyl]-5-phenyl-3,4,5,6-tetrahydro-2H-1,4-oxazin-2-one (0.78 g, 2.3 mmol) in anhydrous dioxane (20 mL) was added distilled triethylamine (0.32 mL, 2.3 mmol). The resulting mixture was stirred at room temperature vigorously for 5 days. Water (20 mL) was added and the mixture was extracted with diethyl ether (3×25 mL). The combined organic extracts were washed with brine (50 mL) and dried over MgSO$_4$. The solvents were removed in vacuo and the crude product was purified by flash column chromatography on silica, eluting with petrol, diethyl ether, and methanol (10:10:1) to furnish the title compound as fine colourless needles (0.67 g, 59%); mp 69.0-70.0° C.; $v_{(max)}$ (KBr) 3312 (O—H), 2980 (C—H), 1738 (C=O, lactone), 1701 (C=O, carbamate), 1654 (C=O, amide) cm$^{-1}$; $\delta_H$ (250 MHz, DMSO—O 8.69 (1H, d, J 7.0 Hz, NH), 7.39 (1H, d, J 7.0 Hz, NH), 7.40-7.26 (5H, m, Ph), 5.80-5.74 (1H, m, PhCH), 5.07-5.02 (1H, m, OH), 4.69 (1H, d, J 14.0 Hz, NCH$_2$×1), 4.13-4.04 (2H, m, CH$_3$CH×2), 3.96-3.91 (1H, m, HOCH$_2$), 3.77-3.74 (1H, m, HOCH$_2$), 3.63 (1H, d, 18.0 Hz, NCH$_2$×1), 1.43 (18H, s, f-butyl×2), 1.23 (3H, d, J 13.0 Hz, CH$_3$), 1.12 (3H, d, J 13.0 Hz$_5$CH$_3$); $\delta_c$ (62.5 MHz, DMSO-J) 176.2, 172.0, 170.7, 156.1, 138.3, 129.0, 128.5, 127.5, 80.9, 78.6, 60.2, 57.5, 49.0, 46.7, 28.5, 27.9, 17.4, 16.9: % (CL, NH$_3$), 494 (MH$^+$, 8%), 476 (6%), 376 (35%), 293 (21%), 249 (46%), and 44 (100%); HRMS for $C_{25}H_{40}N_3O_7$ requires 494.2856. found 494.2872. $[\alpha]_D^{20}$ +24.3 (c 1.09 CHCl$_3$).

L-Alanine tert-butyl ester

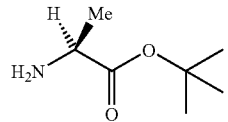

To a mixture of sodium carbonate (875 mg, 8.25 mmol, 5.0 equiv.) in deioned water (10 mL) and diethyl ether (10 mL) was added L-alanine tert-butyl ester hydrochloride (300 mg, 1.65 mmol, 1.0 equiv.). The resulting solution was stirred under an atmosphere of nitrogen for 1 hour. The aqueous phase was extracted with diethyl ether (3×10 mL) and the combined extracts were dried over MgSO$_4$. The solvent was removed in vacuo to settle the title compounds as a colourless oil (200 mg, 84%); $v_{(max)}$ (film) 3377 (N—H), 2978 (C—H), 1729 (C=O) cm$^{-1}$; $\delta_H$ (250 MHz, CDCl$_3$) 3.42 (1H, q, J 7.02 Hz CH), 1.63 (2H, br, NH$_2$), 1.46 (9H, s, (CH$_3$)$_3$), 1.29 (3H, d, J 7.02 Hz, CH$_3$CH); $\delta_c$ (62.5 MHz, CDCl$_3$) 177.1, 81.2, 51.0, 28.4, 21.2; $[\alpha]_D^{20}$ +3.7 (c 0.97 CHCl$_3$), (lit. $[\alpha]_D^{24}$ +2.3 (c 1.00 CHCl$_3$)).

N-Fmoc-(S)-alanyl-N-((1R)-phenyl-2-hydroxylethyl)-(S)-alanyl-(S)-alanine tert-butyl ester

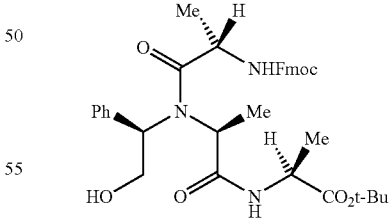

Method 1:

(3S,5R)—N—[N-Fmoc-(S)alanyl]-3-methyl-5-phenyl-3,4,5,6-tetrahydro-2H-1,4-oxazin-2-one (300 mg, 0.62 mmol) and L-alanine tert-butyl ester (135 mg, 0.93 mmol, 1.5 equiv.) were dissolved in anhydrous dichloromethane (14 mL) in a doubly sealed PTFE cylinder and subjected to ultra-high pressure of 19 kbar for 48 hours. After releasing the pressure, the solution was filtered through a short pad of CELITE® diatomaceous earth and removal of solvent from the filtrate in vacuo yielded the crude product which was purified by flash column chromatography on silica, eluting with diethyl ether and dichloromethane (4:1) to furnish the starting material (33) (40 mg, 133%) and the title product as fine colourless needles (122 mg, 31%).
Method 2:

To a solution of L-alanine tert-butyl ester (466 mg (466 mg, 3.21 mmol, 3.0 equvi.) in anhydrous dichloromethane (30 mL) was added trimethyl aluminium (1.87 mL, 3.75 mmol, 2 M in hexane, 3.5 equiv.) under an atmosphere of nitrogen. After 15 minutes, (3S,5R)—N—[N-Fmoc-(S)alanyl]-3-methyl-5-phenyl-3,4,5,6,-tetrahydro-2H-1,4-oxazin-2-one (520 mg, 1.07 mmol) in anhydrous dichloromethane (10 mL) was added. The resulting solution was stirred at room temperature for 24 hours. The reaction was quenched by the addition of water (10 mL) and the organic phase was then washed with saturated copper sulphate (20 mL). The aqueous phase was extracted with diethyl ether (3×20 mL) and the combined organic extracts were washed with brine (50 mL) and dried over $MgSO_4$. The solvents were removed in vacuo and the crude product was purified by flash column chromatography on silica, eluting with diethyl ether and dichloromethane (4:1) to furnish the title compound as fine colourless needles (497 mg, 74%); m.p. 69-71° C.; $v_{(max)}$ (KBr) 3409 (O—H), 2979 (C—H), 1733 (C=O, lactone), 1718 (C=O, carbamate), 1646 (C=O, amide) $cm^{-1}$, $\delta_H$ (250 MHz, OMSO-d) 7.96-7.34 (13H, m, Fmoc×8 and Ph×5), 7.90 (1H, d, /7.41 Hz, NH), 6.10 (1H, s, OH), 5.41-5.33 (1H, m, PhCH), 4.86 (1H, q, /6.76 Hz, $CHCH_3$), 4.40-4.24 (3H, m, $OCH_2CH$), 4.16-4.07 (2H, m, $CH_2OH$), 3.79 (1H, q, /6.95 Hz, $CHCH_3$), 3.63 (1H, q, /6.65 Hz, $CHCH_3$), 1.44 (3H, d, /6.12 Hz, $CHCH_3$), 1.40 (3H, d, /7.19 Hz, $CHCH_3$), 1.27 (9H, s, $C(CHg)_3$), 0.90 (3H, d, /7.42 Hz, $CHCH_3$); $\delta_c$ (62.5 MHz, OMSO-d) 173.5, 171.3, 170.3, 156.6, 144.1, 141.1, 137.6, 129.1, 128.7, 128.0, 127.6, 125.6, 121.7, 120.5, 80.2, 66.2, 60.9, 60.2, 48.7, 47.4, 46.9, 27.8, 17.4, 17.1, 14.9; % (CL, $NH_3$), 775 (100%), 630 ($MH^+$, 25%), 485 (34%), and 408 (17%); HRMS for $C_{36}H_{44}N_3O_7$ requires 630.3170. found 630.3166; $[\alpha]_D^{20}$ −41.2 (c 1.08 $CHCl_3$).

N-Acetyl-N-(1-phenyl-2-hydroxylethyl)alanyl-(S)-alamine tert-butyl ester

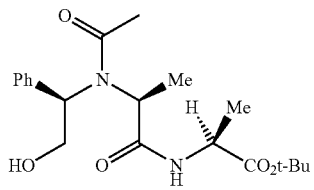

(3S,5R)-4-N-acetyl-3-methyl-5-phenyl-3,4,5,6,-tetrahydro-2H-1,4-oxazin-2-one (68) (220 mg, 0.94 mmol) and L-alanine tert-butyl ester (66) (205 mg, 1.42 mmol, 1.5 equiv.) were dissolved in anhydrous dichloromethane (14 mL) in a doubly sealed PTFE cylinder and subjected to ultra-high pressure of 19 kbar for 48 hours. After releasing the pressure, the solution was filtered through a short pad of CELITE® diatomaceous earth and removal of solvent from the filtrate in vacuo yielded the crude product which was purified by flash column chromatography on silica eluting with diethyl ether and dichloromethane (4:1) to furnish the title product as fine colourless needles (120 mg, 34%); m.p. 38-40° C.; $v_{(max)}$(KBr) 3411 (O—H), 2980 (C—H), 1735 (C=O, lactone), 1646 (C=O, amide) $cm^{-1}$; $\delta_H$ (250 MHz, DMSO-d) 8.06 (0.5H, d, /6.95 Hz, NH×0.5), 7.55-7.24 (5H, m, Ph), 6.54 (0.5H, d, J 6.38 Hz, NH×0.5), 5.82 (0.5H, t, /4.88 Hz, OH×0.5), 5.14-5.06 (1H, m, PhCH), 4.83 (0.5H, t, J 6.56 Hz, OH×0.5), 4.35 (0.5H, q, J 6.99 Hz, $CH_3CH$×0.5), 4.08-4.03 (2H, m, $CH_2OH$), 3.98-3.76 (1.5H, m, $CHCH_3$×0.5 and $CHCH_3$×1), 2.23 (1.5H, s, $COCH_3$), 2.14 (1.5H, s, $COCH_3$), 1.46-1.39 (12H, m, $CHCH_3$×3 and $C(CH_3)_3$×9), 1.19 (1.5H, d, /7.15 Hz, $CHCH_3$×1.5), 0.97 (1.5H, d, J 7.23 Hz, $CHCH_3$×1.5); $\delta_c$ (62.5 MHz, DMSO-d) 171.8, 171.7, 171.0, 170.8, 170.2, 140.0, 138.2, 129.1, 128.2, 128.0, 126.8, 80.7, 62.7, 62.5, 60.8, 56.3, 53.4, 48.8, 48.7, 27.9, 17.5, 16.9, 16.7, 15.2; m/z (CL, $NH_3$), 379 ($MH^+$, 70%), 361 (18%), 305 (20%), 249 (38%), 234 (100%), and 219 (40%); HRMS for $C_{20}H_{31}N_2O_5$ requires 379.2225 found 379.2240; $[\alpha]_D^{20}$ −37.0 (c 1.06 $CHCl_3$).

N-Fmoc-(S)-alanyl-N-((1S)-phenyl-2-hydroxyl-ethyl)-(R)-alanyl-(S)-alanine tert-butyl ester

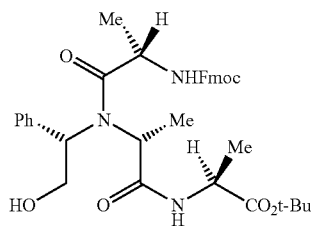

To a solution of L-alanine tert-butyl ester (251 mg, 1.73 mmol, 3.0 equiv.) in anhydrous dichloromethane (25 mL) was added trimethyl aluminium (2.03 mL, 2.03 mmol 2 M in hexane, 3.5 equiv.) under an atmosphere of nitrogen. After 15 minutes, (3R,5S)—N—[N-Fmoc-(S)alanylj-3-methyl-5-phenyl~3,4,5,6,-tetrahydro-2H-1,4-oxazin-2-one (280 mg, 0.58 mmol) in anhydrous dichloromethane (8 mL) was added. The resulting solution was stirred at room temperature for 24 hours. The reaction was quenched by the addition of water (7 mL) and the organic phase was then washed with saturated copper sulphate (15 mL). The aqueous phase was extracted with diethyl ether (3×20 mL) and the combined organic extracts were dried over $MgSO_4$. The solvent was removed in vacuo and the crude product was purified by flash column chromatography on silica, eluting with petrol and diethyl ether (1:4) to furnish the title compound as fine colourless needles (226 mg, 62%); m.p. 87-88° C.; $v_{(max)}$ (KBr) 3410 (O—H), 2980 (C—H), 1727 (C=O), 1654 (C=O) $cm^{-1}$; $\delta_H$ (250 MHz, DMSO-d), 8.35 (0.5H, d, /6.18 Hz, NH) 7.91-7.12 (13H, m, Fmoc×8 and Ph×5), 7.65 (0.5H, d, /7.14 Hz, NH), 7.55 (0.5H, d, /7.32 Hz, NH), 6.39 (0.5H, d, /7.45 Hz, NH), 5.21-5.18 (0.5H, m, PhCH), 5.03-5.01 (0.5H, m, PhCH), 4.94-4.92 (0.5H, m, $NHCHCH_3$), 4.80-4.78 (0.5H, m, $NHCHCH_3$), 4.65-4.62 (0.5H, m, $NCHCH_3$), 4.27-4.18 (3.5H, m, $OCH_2CH$, and $CH_2OH$×0.5), 4.09-3.93 (2.5H, m, $CH_2OH$×1.5 and $NHCHCH_3$), 3.62-3.60 (0.5H, m, $NCHCH_3$×1), 1.44-1.36 (13.5H, s, $(CEb)_3$×9, $CHCH_3$×4.5), 1.23 (1.5H, d, /6.63 Hz, $CHCH_3$), 1.13 (1.5H, d, /7.35 Hz, $CHCH_3$), 0.92 (0.5H, d, /7.07 Hz, $CHCH_3$): $\delta_c$ (62.5 MHz. OMSO-d) 173.4, 172.9, 171.9, 171.6, 169.7, 156.0, 144.2, 144.1, 141.1, 137.2, 129.0, 128.3, 128.0, 127.7, 127.4, 127.3, 125.7, 120.5, 81.2, 80.8, 66.1, 61.6, 55.3, 53.6, 48.6, 48.3, 47.5, 47.0, 27.9, 18.5, 18.2, 17.7, 17.1, 15.4; $^m1_z$ (CL, $NH_3$), 775 (100%), 629 ($M^+$, 36%), 457 (58%), 345 (27%), 231

L-Valine tert-butyl ester

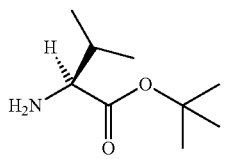

To a mixture of sodium carbonate (1.20 g, 9.54 mmol, 5.0 equiv.) in deioned water (20 mL) and diethyl ether (20 mL) was added L-valine tert-butyl ester hydrochloride (400 mg, 1.71 mmol, 1.0 equiv.). The resulting solution was stirred for 2 hours under an atmosphere of nitrogen. The aqueous phase was extracted with diethyl ether (3×15 mL) and the combined extracts were dried over $MgSO_4$. The solvent was removed in vacuo to settle the title compound as colourless oil (320 mg, 97%); $v_{(max)}$(film) 3393 (N—H), 2967 (C—H), 1728 (C=O) $cm^{-1}$; $\delta_H$(250 MHz, $CDCl_3$) 3.16 (1H, d, J 4.79 Hz, $CHNH_2$), 2.04-1.97 (1H, m, $CH(CH_3)_2$) 1.47 (9H, s, $(CH_3)_3$), 1.38 (2H, s, $NH_2$), 0.97 (3H, d, /6.88 Hz, $(CHg)_2CH\times3$), 0.90 (3H, d, J 6.86 Hz, $(CH_3)_2CH\times3$); $\delta_c$ (62.5 MHz, $CDCl_3$) 175.3, 81.2, 60.7 32.6, 28.5, 19.7, 17.4; $[\alpha]_D^{20}$ +26.4 (c $CHCl_3$), (lit. $[\alpha]_D^{24}$ +25.3 (c 1.00 $CHCl_3$)).

N-Fmoc-(S)-a\any\-N-(1-phenyl-2-hydroxylethyl)-(5)-alanyl-(5)-valine tert-butyl ester (74)

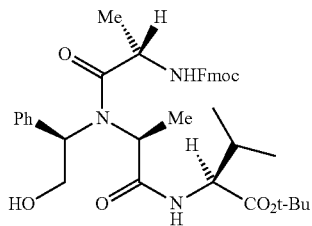

To a solution of L-valine tert-huiyl ester (161 mg, 0.93 mmol, 3.0 equiv.) in anhydrous dichloromethane (10 mL) was added trimethyl aluminium (0.55 mL, 1.09 mmol, 2 M in hexane, 3.5 equiv.) under an atmosphere of nitrogen. After 15 minutes, (3S,5R)—N—[N-Fmoc-(S)alanyl]-3-methyl-5-phenyl-3,4,5,6,-tetrahydro-2H-1,4-oxazin-2-one (150 mg, 0.31 mmol) in anhydrous dichloromethane (5 mL) was added. The resulting solution was stirred at room temperature for 24 hours. The reaction was quenched by the addition of saturated copper sulphate (20 mL) and the mixture was extracted with diethyl ether (3×20 mL). The combined organic extracts were dried over $MgSO_4$. The solvents were removed in vacuo and the crude product was purified by flash column chromatography on silica, eluting with diethyl ether and dichloromethane (9:1) to furnish the title compound as fine colourless needles (128 mg, 63%); m.p. 75.0-76.0° C.; $v_{(max)}$(KBr) 3411 (O—H), 2973 (C—H), 1718 (C=O), 1654 (C=O) $cm^1$; $\delta_H$(250 MHz, DMSO—O 7.96 (1H, d, /7.4 Hz, NH), 7.97-7.29 (13H, m, Fmoc×8 and Ph×5), 5.43 (1H, br, OH), 5.35 (1H, t, /4.2 Hz, PhCH), 4.91 (1H, t, /6.8 Hz, $CHCH_3$), 4.43-4.40 (1H, m, $OCH_2CH$), 4.31-4.21 (2H, m, $OCH_2CH$), 4.20-4.05 (2H, m, $HOCH_2$), 3.79-3.71 (1H, m, $CHCH(CH_3)_2$), 3.70-3.68 (1H, m, $CHCH_3$), 1.81-1.76 (1H, m, $CH(CH_3)_2$), 1.46-1.34 (6H, m, $CHCH_3\times2$) 1.31 (9H, s, f-butyl), 0.68-0.64 (6H, m, $CH(CHg)_2$); $\delta_c$ (62.5 MHz, OMSO-d) 173.1, 170.1, 170.0, 156.4, 144.2, 141.1, 137.6, 129.1, 128.7, 128.3, 128.0, 127.4, 125.7, 124.5, 80.5, 66.4, 63.2, 61.2, 58.1, 53.4, 47.1, 30.1, 27.9, 18.8, 18.4, 17.8, 15.1; $^m1_z$ (CL, $NH_3$), 657 (M+34%), 579 (40%), 427 (59%), 363 (26%), and 244 (100%); HRMS for $C_{38}H_{47}N_3O_7$ requires 657.3404. found 657.3398; $[\alpha]_D^{20}$ –38.7 (c 0.96 $CHCl_3$).

t-Butyl N—[(S)-2-hydroxy-1-phenylethyl]-(5)-valinyl-(5)-alanate

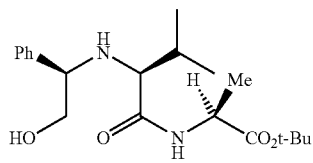

To a solution of L-alanine tert-butyl ester (180 mg, 1.24 mmol, 3.0 equiv.) in anhydrous dichloromethane (10 mL) was added trimethyl aluminium (0.56 mL, 1.12 mmol, 2 M in hexane, 2.7 equiv.) under an atmosphere of nitrogen. After 15 minutes, (3S,5R)-3-wopropyl-5-phenyl-3,4,5,6-tetrahydro-2H-1,4-oxazin-2-one (91 mg, 0.41 mmol) in anhydrous dichloromethane (5 mL) was added. The resulting solution was stirred at room temperature for 24 hours. The reaction was quenched by the addition of saturated copper sulphate (15 mL) and the mixture extracted with diethyl ether (3×15 mL). The combined organic extracts were dried over $MgSO_4$. The solvents were removed in vacuo and the crude product was purified by flash column chromatography on silica, eluting with petrol and diethyl ether (9:1 then 1:20) to furnish the starting material (60 mg, 60%) and the title compound as light yellow oil (50 mg, 33%); $v_{(max)}$(film) 3328 (O—H), 2977 (C—H), 1733 (C=O, ester), 1651 (C=O, amide) $cm^{-1}$; $\delta_H$ (250 MHz, $CDCl_3$) 7.73 (1H, J 8.6 Hz, NH), 7.30-7.18 (5H, m, Ph), 4.54-4.78 (1H, m, $CHCH_3$), 3.74-3.68 (1H, m, PhCH), 3.59-3.50 (2H, m, $HOCH_2$), 2.79 (1H, d, 74.8 Hz, $CHCH(CH_3)_2$), 1.97-1.93 (1H, m, $CH(CH_3)_2$), 1.41 (9H, s, t-butyl), 1.29 (3H, d, /8.7 Hz, $CH_3$), 0.81 (3H, d, J 4.4 Hz, $CH(CH_3)_2$), 0.78 (3H, d, /4.4 Hz, $CH(CH_3)_2$); $\delta_c$ (62.5 MHz, $CDCl_3$) 174.0, 140.8, 128.8, 128.1, 127.7, 125.9, 82.7, 67.6, 66.9, 64.6, 48.4, 31.8, 28.4, 20.0, 19.2, 18.2, $^m1_z$ (CL, $NH_3$), 365 ($MH^+$, 52%), 339 (29%), 333 (76%), 291 (28%), 277 (100%) and 263 (10%); HRMS for $C_{20}H_{33}N_2O_4$ requires 365.2432. found 365.2430. $[\alpha]_D^{20}$ –80.2 (c 0.98 $CHCl_3$).

Potassium N-benzylidenyl-(S)-valinate

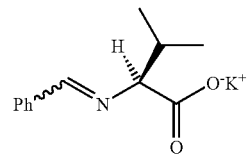

To a solution of potassium hydroxide (958 mg, 17.10 mmol) in methanol (15 mL) was added L-valine (2.00 g, 17.10 mmol). The resulting solution was stirred under nitrogen for 3 hours. The solvent was removed in vacuo before benzaldehyde (2.61 mL, 25.70 mmol 2.0 equiv.) in anhydrous pentane (30 mL) was added and the mixture was azeotropic distillated under nitrogen for 8 hours. The precipitate was collected and dried in high vacuo to furnish the title compound as a white solid (3.85 g, 93%), $V(m_{ax})$ (KBr) 2956 (C—H), 1594 (C=O) $cm^{-1}$; $\delta_H$ (250 MHz, OMSO-d), 8.19 (1H, s, CH=N), 7.75-7.71 (2H, m, Ph×2), 7.44-7.40 (3H, m, Ph×3), 3.26 (1H, d, J 7.24, $CHCH(CH_3)_2$), 2.21 (1H, m, $CHCH(CH_3)_2$), 0.86 (3H, d, J 6.72 Hz, $CHCH(CH_3)_2\times3$), 0.79 (3H, d, /6.72 Hz, CHCH(CH$_3$)$_2$×3); δ$_c$ (62.5 MHz, DMSO-d) 174.7, 159.0, 137.1, 130.3, 128.8, 128.1, 84.8, 31.4, 20.8, 19.5.

N—[N-Fmoc-(S)-alanyl)]-3(S')-isopropyl-5(R,S)-phenyl oxazolidinone

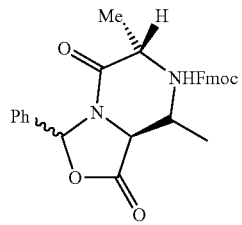

To the stirring suspension of potassium N-benzylidenyl-5-valinate (122 mg, 0.50 mmol) in anhydrous dichloromethane (20 mL) was added Fmoc-L-alanine acid chloride (166 mg, 0.50 mmol) under nitrogen at 0° C. The resulting mixture was stirred for 4 hours at 0° C. and for another 12 hours at room temperature. The solvent was removed in vacuo and the crude product was purified by flash column chromatography on silica, eluting with petrol:diethyl ether (1:1) to furnish the title compound as fine colourless needles (174 mg, 70%); m.p. 69.0-71.5° C.; v$_{(max)}$ (KBr) 3400 (N—H), 2966 (C—H), 1802 (C=O, lactone), 1718 (C=O, carbamate), 1674 (C=O, amide) cm$^1$; δ$_H$ (250 MHz, OMSO-d) 7.70-7.17 (13H, m, Fmoc×8 and Ph×5), 6.45-6.43 (0.3H, m, PhCH× 0.3), 5.36-5.28 (0.7H, m, PhCH×0.7), 4.64-4.47 (1H, m, CHCH$_3$×0.7 and CHCH(CH$_3$)$_2$×0.3), 4.47-4.09 (3H, m, CHCH$_2$), 4.01-3.82 (1H, m, CHCH$_3$×0.3 and CHCH(C$_3$)$_2$× 0.7), 2.83-2.55 (0.3H, m, CH(CH$_3$)$_2$×0.3), 2.20-2.05 (0.7H, m, CH(CH$_3$)$_2$×0.7), 1.43-1.40 (3H, m, CHCH$_3$), 1.26-1.13 (3H, m, CH(CHs)$_2$×0.7) 1.02-0.91 (3H, m, CH(CH$_3$)$_2$×3), 0.87-0.80 (3H, m, CHCH$_3$); δ$_c$ (62.5 MHz, CDCl$_3$) 177.5, 171.3, 169.5, 166.1, 156.0, 144.1, 141.7, 136.3, 131.7, 130.6, 130.2, 129.1, 128.2, 127.5, 127.0, 125.5, 120.4, 91.5, 70.2, 67.5, 61.8, 49.3, 47.5, 46.2, 34.2, 31.1, 30.7, 19.3, 18.9, 18.3, 17.7, 16.7; % (Cl, NH$_3$), 498 (M$^+$, 35%), 476 (47%), 463 (44%), 425 (23%), and 413 (100%); HRMS for C$_{30}$H$_{30}$N$_2$O$_5$ requires 498.2155. found 498.2151.

t-Butyl Fmoc-(S)-ala-(S)-val-(S)-alanate (79)

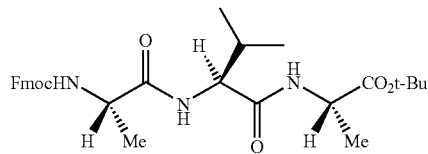

To a solution of L-alanine tert-butyl ester (114 mg, 0.78 mmol, 3.0 equiv.) in anhydrous dichloromethane (10 mL) was added trimethyl aluminium (0.46 mL, 0.91 mmol, 2 M in hexane, 3.5 equiv.) under an atmosphere of nitrogen. After 15 minutes, N—[N-Fmoc-(S)-alanyl)]-3(S)-wopropyl-5(R,S)-phenyl oxazolidinone (130 mg, 0.26 mmol) in anhydrous dichloromethane (5 mL) was added. The resulting solution was stirred at room temperature for 24 hours. The reaction was quenched by the addition of saturated copper sulphate (20 mL) and the mixture was extracted with diethyl ether (3×20 mL). The combined organic extracts were dried over MgSO$_4$. The solvents were removed in vacuo and the crude product was purified by flash column chromatography on silica, eluting with petrol:diethyl ether (1:9) to furnish the title compound as fine colourless needles (76 mg, 54%); mp 153.0-155.0° C.; v$_{(max)}$ (KBr) 3292 (N—H), 2974 (C—H), 1734 (C=O, ester), 1696 (C=O, carbamate), 1645 (C=O, amide) cm$^{-1}$; δ$_H$ (250 MHz, DMSO-d) 8.37 (0.5H, d, /6.42 Hz, NH), 8.18 (0.5H, d, 6.81 Hz. NH), 7.95 (0.5H, d, J 7.56 Hz, NH×0.5), 7.63 (0.5H, d, /7.48 Hz, NH×0.5), 7.96-7.35 (8H, m, Fmoc), 4.31-4.13 (5H, m, CHCH$_3$×2 and CHCH$_2$), 2.03 (1H, q, /6.57 Hz, CH(CH$_3$)$_2$), 1.42 (9H, s, f-butyl), 1.28-1.25 (6H, m, 2×CH$_3$) 0.94-0.85 (6H, m, CH(CHb)$_2$); δ$_c$ (62.5 MHz, DMSO-J) 173.1, 172.6, 171.9, 170.8, 156.1, 144.1, 141.1, 128.0, 127.4, 125.6, 120.5, 80.7, 66.0, 57.4, 57.0, 50.4, 48.7, 47.0, 31.5, 31.0, 30.8, 27.9, 19.5, 18.7, 18.3, 17.9, 17.4, 17.2; $^m$1$_z$ (CL, NH$_3$), 537 (M$^+$, 12%), 502 (100%), 464 (50%), 426 (21%), and 414 (86%); HRMS for C$_{30}$H$_{39}$N$_3$O$_6$ requires 537.2829. found 537.2836. [α]$_D$ −6.2 (c 0.57 CHCl$_3$).

N—[N-Fmoc-(S)-valinyl)]-3(S)-isopropyl-5(R,S)-phenyl oxazolidinone

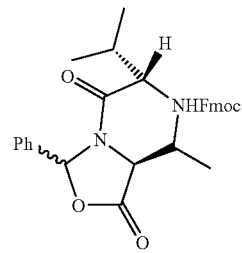

To the stirring suspension of potassium N-benzylidenyl-(S)-valinate (123 mg, 0.46 mmol) in anhydrous dichloromethane (20 mL) was added Fmoc-L-valine acid chloride (164 mg, 0.46 mmol) under nitrogen at 0° C. The resulting mixture was stirred for 4 hours at 0° C. and for another 12 hours at room temperature. The solvent was removed in vacuo and the crude product was purified by flash column chromatography on silica, eluting with petrol:diethyl ether (3:2) to furnish the title compound as fine colourless needles (183 mg, 75%); mp 76.0-78.0° C.; v$_{(max)}$ (KBr) 3326 (N—H), 2966 (C—H), 1802 (C=O, lactone), 1722 (C=O, carbamate), 1663 (C=O, amide) cm$^{-1}$; δ$_H$ (250 MHz, DMSO-d) 7.81-7.11 (14H, m, NH×1, Fmoc×8 and Ph×5), 6.4 (0.5H, s, PhCH×0.5), 4.98 (0.5H, s, PhCH×0.5), 4.48-4.76 (5H, m, CHCH(CH$_3$)$_2$×2 and CHCH$_2$×3), 2.57-2.54 (1H, m, CH(CH$_3$)$_2$), 2.24-2.10 (1H, m, CH(CHs)$_2$), 1.28-0.63 (12H, m, CH(CH$_3$)$_2$×2); δ$_c$ (62.5 MHz, DMSO-d) 170.3, 170, 169.7, 156.9, 144.1, 141.0, 137.5, 130.9, 129.9, 129.5, 128.5, 128.0, 127.7, 127.4, 125.8, 120.5, 90.6, 66.2 61.3, 60.9, 58.3, 46.9, 34.7, 32.6, 30.8, 30.3, 19.7, 18.7, 18.3, 17.2, 16.7, 16.4; % (CL, NH$_3$), 526 (M$^+$, 10%), 331 (40%), 230 (7%) and 178 (100%); HRMS for C$_{32}$H$_{34}$N$_2$O$_5$ requires 526.2459. found 526.2466.

Tri-L-alanine

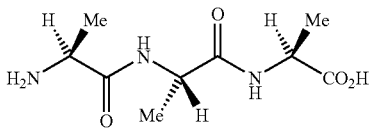

To a solution of N-Fmoc-(S)-alanyl-N-((1R)-phenyl-2-hydroxyethyl)-(S)-alanyl-(S)-alanine tert-butyl ester (235 mg, 0.37 mmol) and tert-butanol (0.12 mL, 1.20 mmol, 3.0 equiv.) in liquid ammonia (15 mL) and anhydrous tetrahydrofuran (10 mL) was added lithium (23 mg, 3.70 mmol, 10.0 equiv.) at −78° C. under an atmosphere of nitrogen. The resulting solution was stirred until the blue colour was disappeared and then warmed to room temperature to evaporate all the liquid ammonia. A mixture of water (15 mL) and diethyl ether (10 mL) was added and the aqueous phase was extracted with diethyl ether (3×10 mL). Water was removed in vacuo and the crude product purified first by acidic ion exchange chromatography and then by flash column chromatography on silica, eluting with methanol and water (7:3) to furnish the title compound as fine colourless needles (71 mg, 84%), $v_{(max)}$ (KBr) 3276 (N—H), 2985 (C—H), 1645 (C=O), 1592 (C=O), 1531 (C=O) cm$^{-1}$; $\delta_H$ (250 MHz, D$_2$O), 4.53 (1H, q, /9.37, CH), 4.03 (2H, q, /7.22 Hz, CH×2), 1.23 (3H, d, J 7.14, CH$_3$), 1.09 (3H, d, J 7.21, CH$_3$), 1.02 (3H, d, /7.24 Hz, CH$_3$); $\delta_c$ (62.5 MHz. D$_2$O) 180.1, 173.9, 170.9, 51.3, 50.1, 49.2, 17.7, 16.9, 16.7; $^m1_z$ (CL, NH$_3$), 231 (M$^+$, 40%), 230 (100%), and 228 (35%); HRMS for C$_9$H$_{17}$N$_3$O$_4$ requires 231.1215 found 231.1209; $[\alpha]_D^{20}$ −72.8 (c 1.01 H$_2$O) (commercial one $[\alpha]_D 20^D$ −73.2 (c 1.02 H$_2$O)).

(5S)-3-Methyl-5-phenyl-5,6-dihydro-2H-1,4-oxazin-2-one (35)[61]

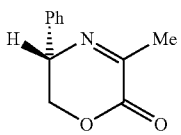

(S)-2-phenylglycinol (3.00 g, 21.9 mmol, 1.0 equiv.) (34) and ethyl pyruvate (2.67 mL, 24.1 mmol, 1 equiv.) were refluxed in trifluoroethanol (50 mL) over activated 4 molecular sieves (8.00 g) for 24 hours. Filtration through a short pad of CELITE® diatomaceous earth and removal of solvent from the filtrate in vacuo delivered the crude product which was purified by flash column chromatography on silica, eluting with petrol and diethyl ether (7:3) to furnish the title compound as a white solid (1.83 g, 44%); m.p. 70.0-71.0° C. (lit 71.0-72.0° C.); $v_{(max)}$(KBr) 3007 (C—H), 1735 (C=O), 1640 (C=N) cm$^{-1}$; $\delta_H$ (250 MHz, CDCl$_3$) 7.45-7.32 (5H, m. Ph), 4.88-4.81 (1H, m, PhCH), 4.56 (1H, dd, J 4.49 Hz, T 9.48 Hz, 6β-H), 4.25 (1H, dd J 13.01 Hz, T 14.99 Hz, 6α-H), 2.41 (3H, s, CH$_3$); $\delta_c$ (62.5 MHz, CDCl$_3$) 160.7, 155.9, 137.2, 129.4, 128.7, 127.5, 71.9, 60.1, 22.2; m/z (CL, NH$_3$), 189 (M$^+$, 25%), 159 (12%), 130 (24%), 104 (100%), 90 (21%), and 78 (6%); HRMS for C$_{11}$H$_{11}$NO$_2$ requires 189.0787 found 189.0782. $[\alpha]_D^{20}$ +253.0 (c 0.98 CHCl$_3$) (the enantiomer lit. $[\alpha]^{D20}$ −237.1 (c 1.11 CHCl$_3$)).

(3R,5S)-3-Methyl-5-phenyl-3,4,5,6-tetrahydro-2H-1,4-oxazin-2-one (36)

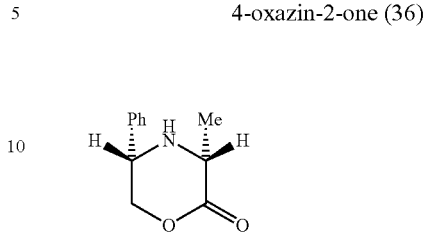

To a solution of (5S)-3-methyl-5-phenyl-5,6-dihydro-2H-1,4-oxazin-2-one (35) (1.70 g, 9.0 mmol, 1.0 equiv.) in anhydrous dichloromethane (60 mL) under an atmosphere of nitrogen was added PtO$_2$ (170 mg, 0.1 equiv.). The mixture was consecutively degassed and purged three times with hydrogen and then stirred for 5 hours under an atmosphere of hydrogen. Filtration through a short pad of CELITE® diatomaceous earth and removal of solvent from the filtrate in vacuo yielded the crude product which was purified by recrystallization from dichloromethane, diethyl ether and hexane to furnish the title compound as a colourless needles (1.26 g, 74%); m.p. 81.0-82.0° C. (lit. m.p. 81.0-82.0° C.); $v_{(max)}$(KBr) 3314 (N—H), 2981 (C—H), 1736 (C=O), cm$^{-1}$, $\delta_H$ (250 MHz, CDCl$_3$) 7.43-7.26 (5H, m, Ph); 4.42-4.23 (3H, m, CHCH$_2$), 3.88 (1H, q, /6.76 Hz, CHCH$_3$), 1.80 (1H, br. NH), 1.50 (3H, d, J 6.76 Hz, CH$_3$); $\delta_c$ (62.5 MHz, CDCl$_3$) 170.7, 138.1, 129.3, 129.1, 127.5, 75.4, 58.2, 55.4, 19.0; m/z (CL, NH$_3$), 192 (MH$^+$, 30%), 147 (68%), 132 (64%), 104 (100%), and 91 (10%); HRMS for C$_{11}$H$_{13}$NO$_2$ requires 192.1025 found 192.1019. $[\alpha]_D^{20}$ +88.8 (c 0.96 CHCl$_3$) (lit. $[\alpha]_D^{20}$ +92.3 (c 0.84 CHCl$_3$)).

(3R,5S)—N—[N-Fmoc-(S)alanyl]-3-methyl-5-phenyl-3,4,5,6,-tetrahydro-2H-1,4-oxazin-2-one (37)

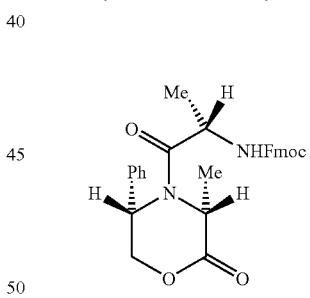

To a vigorously stirred mixture of (3R,5S)-3-methyl-5-phenyl-3,4,5,6-tetrahydro-2H-1,4-oxazin-2-one (36) (500 mg, 2.62 mmol), Na$_2$CO$_3$ (1.40 g, 13.3 mmol, 5.0 equiv.) in 1:1 dichloromethane and water (40 mL) was added N-Fmoc-L-alanine acid chloride (1.04 g, 3.14 mmol, 1.2 equiv.) in dichloromethane (10 mL) dropwise over 5 min. The resulting solution was stirred for 2 hours. The aqueous phase was extracted with dichloromethane (3×15 mL). The combined extracts were washed with saturated Na$_2$CO$_3$ (50 mL), water (2×30 mL), brine (50 mL) and dried over MgSO$_4$. The solvents were removed in vacuo and the crude material was purified by flash column chromatography on silica, eluting with petrol and diethyl ether (1:4) to furnish the title compound as fine colourless needles (1.02 g, 80%); m.p. 87-88° C.; $v_{(max)}$ (KBr) 3323 (N—H), 2982 (C—H), 1761 (C=O, lactone), 1717 (C=O, carbamate), 1656 (C=O, amide)

cm$^{-1}$; δ$_H$ (400 MHz, DMSO-J, 110° C.) 7.84-7.29 (13H, m, Fmoc×8, Ph×5), 7.08 (1H, br, NH), 5.54 (1H, t, /5.88 Hz, PhCH), 4.96 (1H, q, /7.11 Hz, NCHCH$_3$); 4.68-4.60 (2H, m, PhCHCH$_2$), 4.41-4.32 (3H, m, CHCH$_3$NH×1, OCH$_2$CH×2), 4.22 (1H, t, /6.72 Hz OCH$_2$CH), 1.45 (3H, d, /7.15 Hz$_5$ NCHCH$_3$), 1.08 (3H, d, /6.71 Hz, CHCH$_3$NH); δ$_c$ (62.5 MHz, OMSO-d) 174.0, 172.8, 170.4, 169.6, 156.3, 144.1, 141.1, 137.7, 129.4, 128.7, 128.0, 127.4, 127.3, 127.1, 125.6, 120.5, 68.8, 66.0, 55.5, 55.3, 52.2, 51.4, 50.0, 47.2, 20.5, 18.6, 17.7, 17.1; '7$_z$ (C.I., NH$_3$), 485 (MH$^+$, 12%), 431 (8%), 381 (7%), 281 (15%) and 149 (100%); HRMS for C$_{29}$H$_{29}$N$_2$O$_5$ requires 485.2069. found 485.2076; [α]$_D^{20}$ +22.2 (c 0.94 CHCl$_3$).

N-Fmoc-(S)-alanyl-N-((1S)-phenyl-2-hydroxyl-ethyl)-(R)-alanyl-(S)-alanine tert-butyl ester (71)[48]

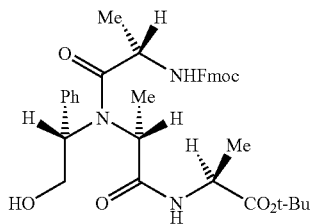

To a solution of L-alanine tert-butyl ester (66) (251 mg, 1.73 mmol, 3.0 equiv.) in anhydrous dichloromethane (25 mL) was added trimethyl aluminium (2.03 mL 2.03 mmol, 2 M in hexane, 3.5 equiv.) under an atmosphere of nitrogen. After 15 minutes, (3R,5S)—N—[N-Fmoc-(S)alanyl]-3-methyl-5-phenyl-3,4,5,6-tetrahydro-2H-1,4-oxazin-2-one (37) (280 mg, 0.58 mmol) in anhydrous dichloromethane (8 mL) was added. The resulting solution was stirred at room temperature for 24 hours. The reaction was quenched by the addition of water (7 mL) and the organic phase was then washed with saturated copper sulphate (15 mL). The aqueous phase was extracted with diethyl ether (3×20 mL) and the combined organic extracts were dried over MgSO$_4$. The solvent was removed in vacuo and the crude product was purified by flash column chromatography on silica, eluting with petrol and diethyl ether (1:4) to furnish the title compound as fine colourless needles (226 mg, 62%); m.p. 87-88° C., ν$_{(max)}$ (KBr) 3410 (O—H), 2980 (C—H), 1727 (C=O), 1654 (C=O) cm$^1$, δ$_H$ (250 MHz, OMSO-d), 8.35 (0.5H, d, /6.18 Hz, NH) 7.91-7.12 (13H, m, Fmoc×8 and Ph×5), 7.65 (0.5H, d, /7.14 Hz, NH), 7.55 (0.5H, d, /7.32 Hz, NH), 6.39 (0.5H, d, /7.45 Hz, NH), 5.21-5.18 (0.5H, m, PhCH), 5.03-5.01 (0.5H, m, PhCH), 4.94-4.92 (0.5H, m, NHCHCH$_3$), 4.80-4.78 (0.5H, m, NHCHCH$_3$), 4.65-4.62 (0.5H, m, NCHCH$_3$), 4.27-4.18 (3.5H, m, OCH$_2$CH, and CH$_2$OH×0.5), 4.09-3.93 (2.5H, m, CH$_2$OH×1.5 and NHCHCH$_3$), 3.62-3.60 (0.5H, m, NCHCH$_3$×1), 1.44-1.36 (13.5H, s, (CHa)$_3$×9, CHCH$_3$×4.5), 1.23 (1.5H, d, /6.63 Hz, CHCH$_3$), 1.13 (1.5H, d, /7.35 Hz, CHCH$_3$), 0.92 (1.5H, d, /7.07 Hz, CHCH$_3$); 6, (62.5 MHz, OMSO-d) 173.4, 172.9, 171.9, 171.6, 169.7, 156.0, 144.2, 144.1, 141.1, 137.2, 129.0, 128.3, 128.0, 127.7, 127.4, 127.3, 125.7, 120.5, 81.2, 80.8, 66.1, 61.6, 55.3, 53.6, 48.6, 48.3, 47.5, 47.0, 27.9, 18.5, 18.2, 17.7, 17.1, 15.4; % (CL, NH$_3$), 775 (100%), 629 (M$^+$, 36%), 457 (58%), 345 (27%), 231 (33%) and 178 (100%); HRMS for C$_{36}$H$_{43}$N$_3$O$_7$ requires 629.3092. found 629.3093; [α]$_D^{20}$ +14.20 (c 1.15 CHCl$_3$).

LDL-alanine

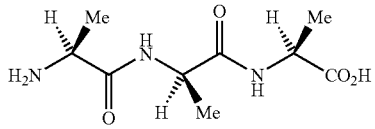

To a solution of N-Fmoc-(S)-alanyl-N-((1R)-phenyl-2-hydroxylethyl)-(R)-alanyl-(S)-alanine tert-butyl ester (235 mg, 0.37 mmol) and tert-butanol (0.12 mL, 1.20 mmol, 3.0 equiv.) in liquid ammonia (15 mL) and anhydrous tetrahydrofuran (10 mL) was added lithium (23 mg, 3.70 mmol, 10.0 equiv.) at −78° C. under an atmosphere of nitrogen. The resulting solution was stirred until the blue colour disappeared and then allowed to warm to room temperature to evaporate off the liquid ammonia. A mixture of water (15 mL) and diethyl ether (10 mL) was added and the aqueous phase was extracted with diethyl ether (3×10 mL). Water was removed in vacuo and the crude product purified first by acidic ion exchange chromatography and then by flash column chromatography on silica, eluting with methanol and water (7:3) to furnish the title compound as fine colourless needles.

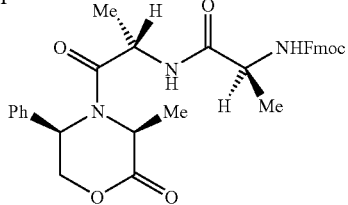

To a solution of (3S,5R)—N—[N-Fmoc-(S)alanyl]-3-methyl-5-phenyl-3,4,5,6,-tetrahydro-2H-1,4-oxazin-2-one (33) (1.00 g, 2.06 mmol, 1.0 equiv.) in anhydrous tetrahydrofuran (40 mL) was added 1,8-diazabicyclo[5.4.0]-undec-7-ene (0.03 mL, 0.21 mmol, 0.1 equiv.) under an atmosphere of nitrogen. The resulting solution was stirred at room temperature for 3.5 hours before N,N-diisopropylethylamine (0.40 mL, 2.26 mmol, 1.1 equiv.), N-Fmoc-L-alanine (0.76 g, 2.46 mmol, 1.2 equiv.) and bromotripyrrolidinophosphonium hexafluorophosphate (1.21 g, 2.46 mmol, 1.2 equiv.) were added. The resulting solution was stirred for another 18 hours during which time a white precipitate was formed. The mixture was filtered through a short pad of CELITE® diatomaceous earth and removal of solvent from the filtrate in vacuo yielded the crude product which was purified by flash column chromatography on silica, eluting with dichloromethane and diethyl ether (3:7) to furnish the title product as a white powder (0.96 g, 86%); m.p. 100.0-101.0° C.; ν$_{(max)}$(KBr) 3311 (N—H), 2981 (C—H), 1741 (C=O), 1718 (C=O), 1647 (C=O) cm$^{-1}$; δ$_H$ (250 MHz, DMSO-d) 7.79 (1H, /6.70 Hz, NH), 7.68-7.07 (13H, m, Fmoc×8, Ph×5), 7.32 (1H, J 7.85 Hz, NH), 5.27 (1H, br, PhCH), 5.16-4.96 (1H, m, PhCHCH$_2$×1), 5.16-4.96 (1H, m, PhCHCH$_2$×1), 4.64-4.62 (1H, m, CHCH$_3$), 4.55-4.51 (1H, m, CHCH$_3$), 4.35-4.32 (1H, m, OCH$_2$CH), 4.00 (2H, m, OCH$_2$CH), 3.89-3.80 (1H, m, CHCH$_3$), 0.98 (3H, d, J 13.92 Hz, CHCH$_3$), 0.93 (3H, br, CHCH$_3$), 0.62 (3H, d, /6.89 Hz, CHCH$_3$); δ$_c$ (62.5 MHz, DMSO-d) 172.8, 171.6, 170.0, 156.0, 144.2, 141.1, 136.3, 128.9, 128.3, 128.0, 127.4, 126.8, 125.7, 120.4, 69.1, 66.0, 52.9, 50.6, 49.9, 47.0, 30.8, 20.9, 18.5, 17.8; m/z (CL, NH$_3$) 231 (M$^+$, 40%), 230 (100%), and 228 (35%); HRMS for C$_{32}$H$_{33}$N$_3$O$_6$ requires 555.2369 found 231.1209; [α]$_D^{20}$ −31.3 (c 0.90 CHCl$_3$).

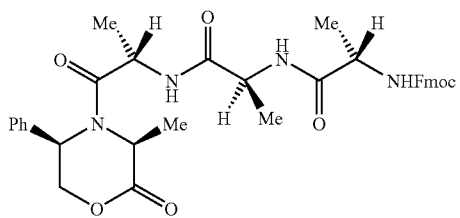

To a solution of (3S,5R)—N—[N-Fmoc-(S)alanyl-(S)-alanine]-3-methyl-5-phenyl-3,4,5,6-tetrahydro-2H-1,4-oxazin-2-one (49) (114 mg, 0.206 mmol, 1.0 equiv.) in anhydrous tetrahydrofuran (5 mL) was added 1,8-diazabicyclo[5.4.0]-undec-7-ene (0.015 mL, 0.103 mmol 0.5 equiv.) under an atmosphere of nitrogen. The resulting solution was stirred at room temperature for 5 hours before N,N-diisopropylethylamine (0.026 mL, 0.144 mmol, 0.7 equiv.), N-Fmoc-L-alanine (76 mg, 0.246 mmol, 1.2 equiv.) and bromotripyrrolidinophosphonium hexafluorophosphate (0.121 g, 0.246 mmol, 1.2 equiv.) were added. The resulting solution was stirred for another 19 hours during which time a white precipitate was formed. The mixture was filtered through a short pad of CELITE® diatomaceous earth and removal of solvent from the filtrate in vacuo yielded the crude product which was purified by flash column chromatography on silica, eluting with dichloromethane and acetone (7:3) to furnish the title product as a white powder. (89 mg, 68%); m.p. 118.0-120.0° C.; $v_{(max)}$(KBr) 3316 (N—H), 2985 (C—H), 1738 (C=O), 1708 (C=O), 1647 (C=O) cm$^{-1}$; $\delta_H$ (250 MHz, DMSO-d) 8.00 (1H, d, /7.28 Hz, NH), 7.91-7.30 (13H, m, Fmocx8, Phx5), 7.52 (1H, d, /7.58 Hz, NH), 5.48 (1H, br, PhCH), 5.32-5.02 (1H, m, PhCHCH$_2$), 4.88-4.85 (1H, m, CHCH$_3$), 4.74-4.69 (1H, m, CHCH$_3$), 4.56 (1H, br, OCH$_2$CH), 4.26-4.27 (2H, m, OCH$_2$CH), 4.03 (1H, t, /7.25 Hz, CHCH$_3$), 3.63-3.58 (0.5H, m, CHCH$_3$), 3.14-3.12 (0.5H, m, CHCH$_3$), 1.26-0.97 (12H, m, CHCH$_3$x4); $\delta_c$ (62.5 MHz, DMSO-d) 172.5, 172.2, 171.6, 170.0, 156.0, 144.2, 141.1, 136.5, 128.9, 128.3, 128.0, 127.4, 126.7, 125.7, 120.5, 65.9, 56.2, 53.9, 53.0, 47.9, 46.0, 42.2, 32.5, 31.0, 29.9, 18.5, 17.8, 17.1, 12.9; % (CL, NH$_3$); HRMS for C$_{35}$H$_{38}$N$_4$O$_7$, requires 626.2741 found; $[\alpha]_D^{20}$ −27.2 (c 1.04 acetone).

$^1$H-NMR data obtained for Tri-L-alanine made according to the invention with commercial tri-L-alanine was compared with excellent results.

While this invention has been particularly shown and described with references to preferred embodiments thereof, it will be understood by those skilled in the art that various changes in form and details may be made therein without departing from the scope of the invention encompassed by the appended claims.

The invention claimed is:
1. A process for the production of a compound of formula (Ic):

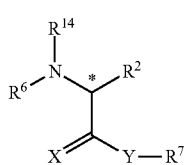

(Ic)

comprising reaction of a compound of formula (VII)

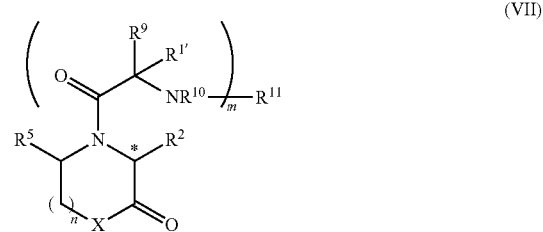

(VII)

with a compound of formula (III)

HY—R$^7$ (III)

wherein X is O, S, or NR$^8$, where R$^8$ is C$_{1-16}$ alkyl, C$_{6-12}$ aryl or hydrogen;

Y is O, S or NH;

R$^2$ is independently selected from a C$_{1-10}$ branched or straight chain alkyl group, C$_{5-12}$ heteroaryl group or C$_{6-12}$ aryl group, optionally substituted with OR$^{13}$, SR$^{13}$, N(R$^{13}$)$_2$, CO$_2$R$^{13}$, CON(R$^{13}$)$_2$, SO$_2$R$^{12}$, SO$_3$R$^{12}$, phenyl, imidazolyl, indolyl, hydroxyphenyl or NR$^{13}$C(=NR$^{13}$)N(R$^{13}$)$_2$;

wherein each R$^{1'}$ is independently hydrogen or as defined from R$^1$ below;

R$^{14}$ is —[CO—C(R$^{1'}$)(R$^9$)—N(R$^{10}$)]$_m$—(R$^{11}$);

R$^{12}$ is hydrogen, C$_{1-6}$ alkyl, C$_{6-12}$ aryl or N(R$^{13}$)$_2$, wherein each occurrence of R$^{13}$ is independently hydrogen, C$_{1-6}$ alkyl or C$_{6-12}$ aryl, each R$^9$ and R$^{10}$ is independently hydrogen or a group as defined for R$^{1'}$;

or R$^9$ and R$^{10}$ can together form a 4 to 7 membered ring, optionally substituted with OR$^{13}$, SR$^{13}$, N(R$^{13}$)$_2$, CO$_2$R$^{13}$, CON(R$^{13}$)$_2$, C$_{1-10}$ alkyl or C$_{6-12}$ aryl,
wherein said ring can be fully, partially or unsaturated, and wherein the ring may contain one or more heteroatoms selected from O, S or N;

R$^{11}$ is hydrogen or an amino protecting group, wherein the amino protecting group is a benzyloxycarbonyl group, a t-butoxycarbonyl group, a 2-(4-biphenylyl)-isopropoxycarbonyl group, a fluorenylmethoxycarbonyl group, a triphenylmethyl group or a 2-nitrophenylsulphenyl group;

R$^5$ is a C$_{5-12}$ aryl, C$_{5-12}$ heteroaryl or C$_{1-8}$ branched or straight chain alkyl optionally substituted with OR$^{13}$, SR$^{13}$, N(R$^{13}$)$_2$, CO$_2$R$^{13}$, CON(R$^{13}$)$_2$, phenyl, imidazolyl, indolyl, hydroxyphenyl or NR$^{13}$C(=NR$^{13}$)N(R$^{13}$)$_2$ or a linker for attachment of formula (VII) to a resin, wherein the linker is OR$^{13}$, N(R$^{13}$)$_2$, CO$_2$R$^{13}$ or SR$^{13}$, or an alkyl group having 1 to 4 carbons or a C$_{6-12}$ aryl group, said alkyl and aryl groups being optionally substituted with OR$^{13}$, N(R$^{13}$)$_2$, CO$_2$R$^{13}$ or SR$^{13}$;

R$^6$ is hydrogen or

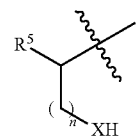

wherein R$^5$ and X are as defined above;

$R^7$ is a group

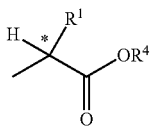

or is independently selected from a $C_{1-10}$ branched or straight chain alkyl group or a $C_{6-12}$ aryl group, optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$ or wherein $R^7$ and Y together form a 4 to 7 membered ring, optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$, wherein said ring can be fully, partially or unsaturated, and wherein the ring may contain one or more heteroatoms in addition to Y, selected from O, S or N; wherein $R^1$ is independently selected from a $C_{1-10}$ branched or straight chain alkyl group, $C_{5-12}$ heteroaryl group or $C_{6-12}$ aryl group optionally substituted with $OR^{13}$, $SR^{13}$, $N(R^{13})_2$, $CO_2R^{13}$, $CON(R^{13})_2$, $SO_2R^{12}$, $SO_3R^{12}$, phenyl, imidazolyl, indolyl, hydroxyphenyl or $NR^{13}C(=NR^{13})N(R^{13})_2$;

$R^4$ is a carboxyl protecting group or hydrogen, wherein the carboxyl protecting group is methyl, ethyl, benzyl, t-butyl or phenyl;

n is 1, 2 or 3, and m is a value selected from 1-100.

2. The process as claimed in claim 1 wherein $R^1$ and $R^2$ are independently selected from $C_1$ alkyl optionally substituted with OH, SH, $CO_2H$, $CONH_2$, phenyl, imidazolyl, indolyl or hydroxyphenyl; $C_2$ alkyl optionally substituted with OH, $CO_2H$, $CONH_2$ or $SCH_3$; $C_3$ alkyl $NHC(=NH)NH_2$ or $C_4$ alkyl optionally substituted with $NH_2$.

3. The process as claimed in claim 1 wherein $R^5$ is a linked resin and the process is carried out on solid phase.

4. The process as claimed in claim 1 wherein the process is carried out in solution.

5. The process as claimed in claim 1, further comprising replacement of the $R^6$ group with hydrogen to form a compound of formula (Ic):

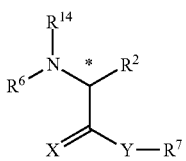

(Ic)

wherein X, Y, $R^2$, $R^7$ and $R^{14}$ are as defined above in claim 1, and wherein $R^6$ is hydrogen.

6. The process as claimed in claim 1 wherein the production of a compound of formula (Ic) occurs without epimerization.

7. The process as claimed in claim 1, wherein the production of a compound of formula (Ic) comprises
(a) converting an amine of formula (IV)

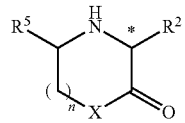

(IV)

to form a compound of formula (VII) via peptide bond formation; and
(b) reacting the compound of formula (VII)

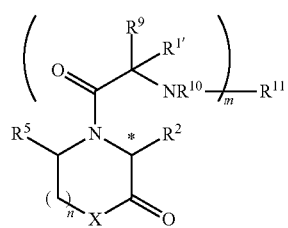

(VII)

with a compound of formula (III).

8. The process of claim 7, wherein the formation of a compound of formula (VII) occurs by reaction of one or more compounds of formula (V)

$$Z-CO-R^3 \quad (V)$$

in a stepwise manner,
wherein $R^3$ is as defined for $R^2$ or is hydrogen, or a group

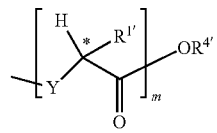

or a group $-C(R^{1'})(R^9)-N(R^{10})(R^{11})$;
Z is hydroxide, halide or azide;
$R^{4'}$ is as defined for $R^4$;
and wherein Y, $R^{1'}$, $R^4$, $R^9$, $R^{10}$ and $R^{11}$ are as defined above in claim 1.

9. The process as claimed in claim 7, wherein the production of a compound of formula (Ic) occurs without epimerization.

10. The process as claimed in claim 7, wherein $R^5$ is a linked resin and the process is carried out on solid phase.

11. The process as claimed in claim 7, wherein the process is carried out in solution.

* * * * *